United States Patent
Farber

(10) Patent No.: US 12,054,696 B2
(45) Date of Patent: Aug. 6, 2024

(54) COMPOSITIONS AND METHODS FOR BREWING SOUR BEER

(71) Applicant: University of the Sciences, Philadelphia, PA (US)

(72) Inventor: Matthew J. Farber, Media, PA (US)

(73) Assignee: Saint Joseph's University, Philadelphia, PA (US)

( * ) Notice: Subject to any disclaimer, the term of this patent is extended or adjusted under 35 U.S.C. 154(b) by 197 days.

(21) Appl. No.: 17/706,365

(22) Filed: Mar. 28, 2022

(65) Prior Publication Data

US 2022/0213417 A1    Jul. 7, 2022

Related U.S. Application Data

(62) Division of application No. 16/632,100, filed as application No. PCT/US2018/043148 on Jul. 20, 2018, now Pat. No. 11,286,445.

(60) Provisional application No. 62/534,770, filed on Jul. 20, 2017.

(51) Int. Cl.
| | |
|---|---|
| *C12N 1/16* | (2006.01) |
| *C12C 11/00* | (2006.01) |
| *C12C 12/00* | (2006.01) |
| *C12N 1/14* | (2006.01) |
| *C12R 1/645* | (2006.01) |

(52) U.S. Cl.
CPC .......... *C12C 12/006* (2013.01); *C12C 11/003* (2013.01); *C12N 1/145* (2021.05); *C12N 1/16* (2013.01); *C12C 2200/05* (2013.01); *C12R 2001/645* (2021.05)

(58) Field of Classification Search
CPC . C12C 12/006; C12C 11/003; C12C 2200/05; C12N 1/145; C12N 1/16
USPC .......................................................... 426/16
See application file for complete search history.

(56) References Cited

U.S. PATENT DOCUMENTS

| | | |
|---|---|---|
| 2006/0257529 A1 | 11/2006 | Sommer et al. |
| 2008/0248158 A1 | 10/2008 | Dörr et al. |
| 2018/0119074 A1 | 5/2018 | Sheppard et al. |

FOREIGN PATENT DOCUMENTS

| | | | |
|---|---|---|---|
| DE | 102009023209 A1 | 2/2011 | |
| WO | 2004072271 A1 | 8/2004 | |
| WO | 2016187021 A1 | 11/2016 | |
| WO | WO-2016187021 A1 * | 11/2016 | ........... C12C 11/003 |
| WO | 2016193465 A1 | 12/2016 | |

OTHER PUBLICATIONS

"Search Results", SEQ ID No. 8, 2021.
"Search Results", SEQ ID No. 9, 2021.
Charron, et al., "Exploring the Northern Limit of the Distribution of *Saccharomyces cerevisiae* and *Saccharomyes paradoxus* in North America", FEMS, Yeast Research, vol. 14, Issue 2, Mar. 1, 2014, pp. 281-288.
Domizio, et al., "*Lachancea thermotolerans* as an alternative yeast for the production of beer", J Inst Brew, vol. 122, Nov. 16, 2016, pp. 599-604.
Gatto, et al., "New Insights into the Variability of Lactic Acid Production in *Lachancea thermotolerans* at the Phenotypic and Genomic Level", Microbiol Res, vol. 238, Jun. 17, 2020, pp. 126525, 1-10.
Gobbi, et al., "*Lachancea thermotolerans* and *Saccharomyces cerevisiae* in simultaneous and sequential co-fermentation; A strategy to enhance acidity and improve the overall quality of winte", Food Microbiol, vol. 33, 2013, pp. 271-281.
Lachance, "Current status ofKluyveromyces systematics", FEMS Yeast Res, vol. 7, 2007, pp. 642-645.
Naumova, et al., "Speciation in the Yeast *Lachancea thermotolerans*: Molecular Genetic Evidence", Doklady Biological Sci, vol. 405, No. 5, 2005, pp. 469-471.
Osburn, et al., "Primary souring: A novel bacteria-free method for sour beer", Food Microbiol, vol. 70, Sep. 14, 2017, pp. 76-84.

* cited by examiner

*Primary Examiner* — Hamid R Badr
(74) *Attorney, Agent, or Firm* — Saul Ewing LLP; Domingos J. Silva; Chihao Wang

(57) ABSTRACT

The present invention relates to the unexpected discovery of a new strain of yeast, dubbed GY7B, which is related to, but genetically and phenotypically distinct from, *Lachancea thermotolerans*. The invention provides methods of brewing sour beer using GY7B, wherein the methods do not require use of lactic acid or lactic acid producing bacteria.

19 Claims, 13 Drawing Sheets
Specification includes a Sequence Listing.

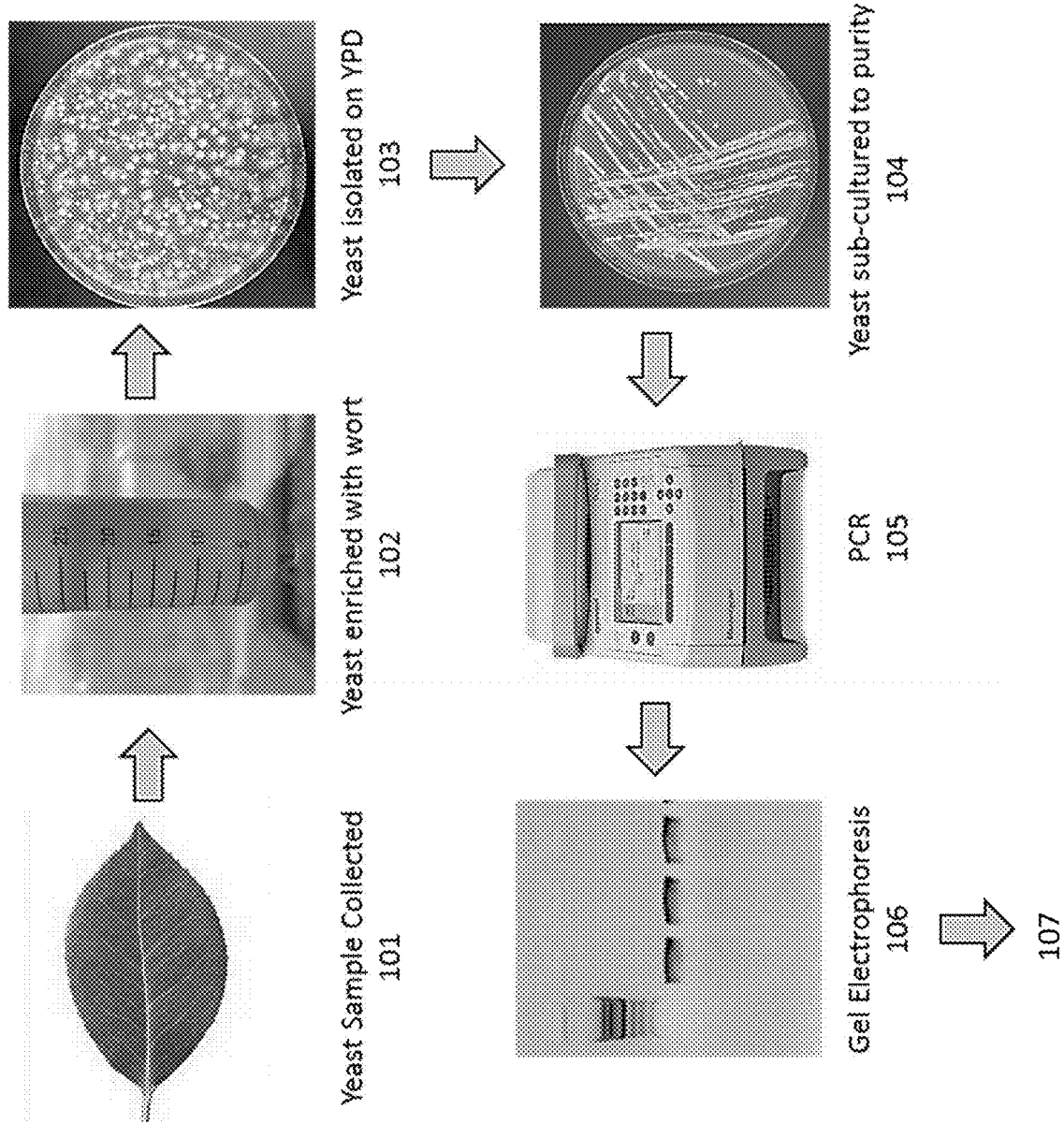

```
SEQ ID NO. 11
Query  121  ATGGAGGGTGAGAATCCGTATGGGAGGAGTCAGTCTAGTCCTATGTAAGTGTTTCGACGA  180
             ||||||||||||||||||||| ||||||| ||||||||||||||||||||||||||||
Sbjct  156  ATGGAGGGTGAGAATCCCGTATGGGCAGGAGTCAGTCTAGTCCTATGTAAGTGCTTCGACGA  215

Query  181  GTCGAGTTGTTTGGATGCAGTCAGTCTAGTGGGTGTAATTCCATGTAAGCTAAGTATTTT  240
             ||||||||||||||||||||||||||||||||| |||||||||||||||||||||||||
Sbjct  216  GTCGAGTGTGTTTGGGATGCCAGTCAGTCTAGTTGGGTGTAAATTCATGTAAGCTAAGTATAT  275

SEQ ID NO. 12
```

BLAST analysis
108

Effect of pH on Y8284

COMPOSITIONS AND METHODS FOR BREWING SOUR BEER

CROSS-REFERENCE TO RELATED APPLICATION

The present application is a division of, and claims priority to, U.S. patent application Ser. No. 16/632,100, filed Jan. 17, 2020, now allowed, which is a 35 U.S.C. § 371 national phase application of, and claims priority to, International Application PCT/US2018/043148, filed Jul. 20, 2018, which claims priority under 35 U.S.C. § 119(e) to U.S. Provisional Application No. 62/534,770, filed Jul. 20, 2017, all of which are incorporated herein by reference in its entirety for all purposes.

DEPOSIT STATEMENT

The GY7B yeast strain was deposited, in accordance with the Budapest Treaty, with the American Type Culture Collection (ATCC®) on Jul. 19, 2018, under Accession Number PTA-125167. In accordance with 37 CFR § 1.808, the depositors assure that all restrictions imposed on the availability to the public of the deposited materials will be irrevocably removed upon the granting of a patent.

SEQUENCE LISTING

The ASCII text file named "368763-7006US2_Replacement_Sequence_Listing.txt" created Feb. 6, 2024, comprising 5.03 Kbytes, is hereby incorporated by reference in its entirety.

BACKGROUND OF THE INVENTION

It is estimated that there are 5.1 million different species of yeast, yet only 1-2% have been characterized and described. Different strains of yeast have differing properties. Examples of commercially useful yeast strain categories include "baker's yeast" (which is a leavening agent) and "brewer's yeast" (which is used for alcoholic fermentation processes). It should be noted that, within each category, specific strains can produce distinct metabolic byproducts, which alter the properties of the food products in which they are incorporated.

In the production of beer, certain styles and brewing techniques lend themselves to a sour character. There exists two primary methods for souring beer in the brewing industry. Food-grade lactic acid may be added directly to the wort or beer, which yields sourness and acidity on the palate but often leads to a crisp, bland flavor. The other method involves the use of Lactic-acid bacteria (LAB), primarily bacteria belonging to genera such as *Lactobacillus* or *Pediococcus*. LAB may be added to wort between the mash and the boil, in a technique called kettle-souring. More fully developed sour flavors require the use of bacteria in the fermenter or during maturation of beer in bright tanks, barrels, or foeders, which can take 2 months to 2 years to fully develop.

There is thus a need in the art for the identification of yeast strains that can be used in the fermentation of sour beer. In certain embodiments, such strains should allow for rapid production of sour beer without the use of lactic acid and/or LAB. This invention addresses these needs.

BRIEF SUMMARY OF THE INVENTION

The invention provides a method of producing a yeast-fermented beverage. The invention further provides a yeast strain able to produce a yeast-fermented beverage with a low pH and a sour taste without the use of lactic acid producing bacteria. The invention further provides compositions comprising a yeast strain contemplated within the invention. The invention further provides a kit comprising a yeast strain contemplated within the invention. The invention further provides use of a yeast strain contemplated within the invention to produce a beer with a low pH and a sour taste. The invention further contemplates use of a kit contemplated within the invention to produce a beer with a low pH and a sour taste.

In certain embodiments, the method comprises fermenting a wort in the presence of a yeast strain able to produce a yeast-fermented beverage with a low pH and a sour taste without the use of lactic acid producing bacteria. In other embodiments, the yeast strain is able to produce a yeast-fermented beverage with a pH of about 4.2 to about 3.3 without the use of lactic acid producing bacteria.

In certain embodiments, the yeast-fermented beverage is beer. In other embodiments, the beer is produced without the use of lactic acid producing bacteria. In yet other embodiments, the beer is produced without the use of lactic acid. In yet other embodiments, the beer has a pH of about 4.2 to about 3.3.

In certain embodiments, the yeast strain is able to reduce the pH of wort to about 3.5 in about 5 days without the use of acid producing bacteria. In other embodiments, the yeast strain belongs to the genus *Lachancea*. In yet other embodiments, the yeast strain is GY7B (deposited with the ATCC under Accession Number PTA-125167 on Jul. 19, 2018). In yet other embodiments, the yeast strain comprises the nucleotide sequence of SEQ ID NO. 8 within the ITS region. In yet other embodiments, the yeast strain comprises the nucleotide sequence of SEQ ID NO. 9 within the actin1 gene. In yet other embodiments, the yeast strain comprises the nucleotide sequence of SEQ ID NO. 8 within the ITS region and the nucleotide sequence of SEQ ID NO. 9 within the actin1 gene.

In certain embodiments, the method produces a yeast-fermented beverage with a pH of about 4.2 to about 3.3. In other embodiments, the wort is fermented in the absence of any acid producing bacteria. In yet other embodiments, the method does not comprise use of lactic acid, or equivalent thereof. In yet other embodiments, lactic acid, or equivalent thereof, is not added to the wort, before, during, and/or after fermentation.

In certain embodiments, the wort is fermented in the absence of any lactic acid producing bacteria. In other embodiments, the wort is fermented in the absence of bacteria belonging to genera *Lactobacillus*. In yet other embodiments, the wort is fermented in the absence of bacteria belonging to genera *Pediococcus*. In yet other embodiments, the wort is fermented in the absence of bacteria belonging to genera *Lactobacillus* and/or *Pediococcus*. In yet other embodiments, the wort comprises malt derived from one or more grains selected from the group consisting of barley, wheat, corn, rye, rice, oats, sorghum, millet, buckwheat, quinoa, and teff.

In certain embodiments, the wort is fermented in the presence of at least one additional yeast strain.

In certain embodiments, the yeast strain is part of a composition further comprising at least one additional yeast selected from the group consisting of a *Saccharomyces* yeast, another *Lachancea* yeast, and a *Brettanomyces* yeast. In other embodiments, the yeast strain is part of a composition further comprising at least one *Saccharomyces* yeast. In yet other embodiments, the yeast strain is part of a composition further comprising at least one additional *Lachancea* yeast. In yet other embodiments, the yeast strain is part of a composition further comprising at least one *Brettanomyces* yeast.

In certain embodiments, the composition further comprises at least one additional yeast. In other embodiments, the at least one additional yeast is selected from the group consisting of a *Saccharomyces* yeast, another *Lachancea* yeast, and a *Brettanomyces* yeast. In yet other embodiments, the at least one additional yeast is a *Saccharomyces* yeast. In yet other embodiments, the at least one additional yeast is another *Lachancea* yeast. In yet other embodiments, the at least one additional yeast is a *Brettanomyces* yeast.

In certain embodiments, the yeast strain is able to produce a yeast-fermented beverage with a pH of about 4.2 to about 3.3 without the use of lactic acid producing bacteria. In other embodiments, the yeast strain is able to reduce the pH of word to about 3.5 in about 5 days without the use of acid producing bacteria.

In certain embodiments, the yeast strain belongs to the genus *Lachancea*. In other embodiments, the yeast strain is GY7B (deposited with the ATCC under Accession Number PTA-125167 on Jul. 19, 2018). In yet other embodiments, the yeast strain comprises the nucleotide sequence of SEQ ID NO. 8 within the ITS region. In yet other embodiments, the yeast strain comprises the nucleotide sequence of SEQ ID NO. 9 within the actin1 gene. In yet other embodiments, the yeast strain comprises the nucleotide sequence of SEQ ID NO. 8 within the ITS region and the nucleotide sequence of SEQ ID NO. 9 within the actin1 gene.

In certain embodiments, the kit comprises a yeast strain contemplated within the invention and one or more items or ingredients suitable to produce a yeast-fermented beverage.

In certain embodiments, the kit comprises yeast strain GY7B (deposited with the ATCC under Accession Number PTA-125167 on Jul. 19, 2018). In other embodiments, the kit further comprises instructional materials comprising instructions for producing a yeast-fermented beverage using yeast strain GY7B. In yet other embodiments, the kit further comprises one or more items or ingredients to produce a yeast-fermented beverage using GY7B;

In certain embodiments, the kit comprises a yeast strain from the genus *Lachancea*, wherein the yeast strain comprises the nucleotide sequence of SEQ ID NO. 8 within the ITS region and/or the nucleotide sequence of SEQ ID NO. 9 within the actin1 gene. In other embodiments, the kit comprises instructional materials comprising instructions for producing a yeast-fermented beverage using the yeast strain. In yet other embodiments, the kit comprises one or more items or ingredients to produce a yeast-fermented beverage using the yeast strain.

In certain embodiments, the one or more items or ingredients comprise prepared wort solution. In other embodiments, the one or more items or ingredients comprise dry malt extract. In yet other embodiments, the one or more items or ingredients comprise one or more grains selected from the group consisting of barley, wheat, corn, rye, rice, oats, sorghum, millet, buckwheat, quinoa, and teff. In yet other embodiments, the one or more items or ingredients comprise at least one additional yeast strain. In yet other embodiments, the one or more items or ingredients comprise one or more varieties of hops. In yet other embodiments, the one or more items or ingredients comprise conditioned brewing water. In yet other embodiments, the one or more items or ingredients comprise one or more sugar adjuncts.

In certain embodiments, the at least one additional yeast strain is selected from the group consisting of *Saccharomyces cerevisiae, Saccharomyces pastorianus, Saccharomyces paradoxus, Saccharomyces eubayanus, Saccharomyces ludwigii, Aureobasidium pullulans, Cyberlindnera saturnus, Hansensiaspora uvarum, Hansensiaspora guilliermondii, Hansensiaspora osmophila, Hansensiasporavineae, Hansenula anomala, Issatchenkia occidentalis, Issatchenkia orientalis, Pichia kluyveri, Pichia caribbica, Pichia fermentans, Pichia kudriavzevii, Pichia Membranifaciens, Rhodotorula mucilaginosa, Torulaspora delbrueckii, Candida colliculosa, Candida shehatae, Candida tropicalis, Candida ethanolica, Candida krusei, Candida magnolia, Candida milleri, Clavispora lusitaniae, Wickerhamomyces subpelliculosus, Wickerhamomyces anomalus, Zygosaccharomyces rouxii, Zygosaccharomyces bailii, Zygosaccharomyces fermentati, Zygosaccharomycesflorentinus, Kluyveromyces lactis, Kluyveromyces marxianus, Lachancea thermotolerans, Brettanomyces bruxellensis, Brettanomyces anomalus, Brettanomyces custersianus, Brettanomyces naardenensis, Brettanomyces nanus, Dekkera bruxellensis,* and *Dekkera anomala*.

In certain embodiments, the at least one additional yeast strain is *Saccharomyces cerevisiae*. In other embodiments, the at least one additional yeast strain is *Saccharomyces pastorianus*. In yet other embodiments, the at least one additional yeast strain is *Saccharomyces paradoxus*. In yet other embodiments, the at least one additional yeast strain is *Saccharomyces eubayanus*. In yet other embodiments, the at least one additional yeast strain is *Saccharomyces ludwigii*. In yet other embodiments, the at least one additional yeast strain is *Aureobasidium pullulans*. In yet other embodiments, the at least one additional yeast strain is *Cyberlindnera saturnus*. In yet other embodiments, the at least one additional yeast strain is *Hansensiaspora uvarum*. In yet other embodiments, the at least one additional yeast strain is *Hansensiaspora guilliermondii*. In yet other embodiments, the at least one additional yeast strain is *Hansensiaspora osmophila*. In yet other embodiments, the at least one additional yeast strain is *Hansensiasporavineae*. In yet other embodiments, the at least one additional yeast strain is *Hansenula anomala*. In yet other embodiments, the at least one additional yeast strain is *Issatchenkia occidentalis*. In yet other embodiments, the at least one additional yeast strain is *Issatchenkia orientalis*. In yet other embodiments, the at least one additional yeast strain is *Pichia kluyveri*. In yet other embodiments, the at least one additional yeast strain is *Pichia caribbica*. In yet other embodiments, the at least one additional yeast strain is *Pichia fermentans*. In yet other embodiments, the at least one additional yeast strain is *Pichia kudriavzevii*. In yet other embodiments, the at least one additional yeast strain is *Pichia Membranifaciens*. In yet other embodiments, the at least one additional yeast strain is *Rhodotorula mucilaginosa*. In yet other embodiments, the at least one additional yeast strain is *Torulaspora delbrueckii*. In yet other embodiments, the at least one additional yeast strain is *Candida colliculosa*. In yet other embodiments, the at least one additional yeast strain is *Candida shehatae*. In yet other embodiments, the at least one additional yeast strain is *Candida tropicalis*. In yet other embodiments, the at least one additional yeast strain is *Candida ethanolica*. In yet other embodiments, the at least one additional yeast strain is *Candida krusei*. In yet other embodiments, the at least one additional yeast strain is *Candida magnolia*. In yet other embodiments, the at least one additional yeast strain is *Candida milleri*. In yet other embodiments, the at least one additional yeast strain is *Clavispora lusitaniae*. In yet other embodiments, the at least one additional yeast strain is *Wickerhamomyces subpelliculosus*. In yet other embodiments, the at least one additional yeast strain is *Wickerhamomyces anomalus*. In yet other embodiments, the at least one additional yeast strain is *Zygosaccharomyces rouxii*. In yet other embodiments, the at least one additional yeast strain is *Zygosaccharomyces bailii*. In yet other embodiments, the at least one additional yeast strain is *Zygosaccharomyces fermentati*. In yet other embodiments, the at least one additional yeast strain is *Zygosaccharomycesflorentinus*. In yet other embodiments, the at least one additional yeast strain is *Kluyveromyces lactis*. In yet other embodiments, the at least one additional yeast strain is *Kluyveromyces marxianus*. In yet other embodiments, the at least one additional yeast strain is *Lachancea thermotolerans*. In yet other embodiments, the at least one additional yeast strain is *Brettanomyces bruxellensis*. In yet other embodiments, the at least one additional yeast strain is *Brettanomyces anomalus*. In yet other embodiments, the at least one additional yeast strain is *Brettanomyces custersianus*. In yet other embodiments, the at least one additional yeast strain is *Brettanomyces naardenensis*. In yet other embodiments, the at least one additional yeast strain is *Brettanomyces nanus*. In yet other embodiments, the at least one additional yeast strain is *Dekkera bruxellensis*. In yet other embodiments, the at least one additional yeast strain is *Dekkera anomala*.

In certain embodiments, the wort comprises hops. In other embodiments, the hops comprises Ahtanum. In other embodiments, the hops comprises Amarillo. In yet other embodiments, the hops comprises Apollo. In yet other embodiments, the hops comprises Cascade. In yet other embodiments, the hops comprises Centennial. In yet other embodiments, the hops comprises Chinook. In yet other embodiments, the hops comprises Citra. In yet other embodiments, the hops comprises Cluster. In yet other embodiments, the hops comprises Columbus. In yet other embodiments, the hops comprises Crystal. In yet other embodiments, the hops comprises Eroica. In yet other embodiments, the hops comprises Galena. In yet other embodiments, the hops comprises Glacier. In yet other embodiments, the hops comprises Greenburg. In yet other embodiments, the hops comprises Horizon. In yet other embodiments, the hops comprises Liberty. In yet other embodiments, the hops comprises Millenium. In yet other embodiments, the hops comprises Mount Hood. In yet other embodiments, the hops comprises Mount Rainier. In yet other embodiments, the hops comprises Newport. In yet other embodiments, the hops comprises Nugget. In yet other embodiments, the hops comprises Palisade. In yet other embodiments, the hops comprises Santiam. In yet other embodiments, the hops comprises Simcoe. In yet other embodiments, the hops comprises Sterling. In yet other embodiments, the hops comprises Summit. In yet other embodiments, the hops comprises Tomahawk. In yet other embodiments, the hops comprises Ultra. In yet other embodiments, the hops comprises Vanguard. In yet other embodiments, the hops comprises Warrior. In yet other embodiments, the hops comprises Willamette. In yet other embodiments, the hops comprises Zeus. In yet other embodiments, the hops comprises Admiral. In yet other embodiments, the hops comprises Brewer's Gold. In yet other embodiments, the hops comprises Bullion. In yet other embodiments, the hops comprises Challenger. In yet other embodiments, the hops comprises First Gold. In yet other embodiments, the hops comprises Fuggles. In yet other embodiments, the hops comprises Goldings. In yet other embodiments, the hops comprises Herald. In yet other embodiments, the hops comprises Northdown. In yet other embodiments, the hops comprises Northern Brewer. In yet other embodiments, the hops comprises Phoenix. In yet other embodiments, the hops comprises Pilot. In yet other embodiments, the hops comprises Pioneer. In yet other embodiments, the hops comprises Progress. In yet other embodiments, the hops comprises Target. In yet other embodiments, the hops comprises Whitbread Golding Variety (WGV). In yet other embodiments, the hops comprises Hallertau. In yet other embodiments, the hops comprises Hersbrucker. In yet other embodiments, the hops comprises Saaz. In yet other embodiments, the hops comprises Tettnang. In yet other embodiments, the hops comprises Spalt. In yet other embodiments, the hops comprises Feux-Coeur Francais. In yet other embodiments, the hops comprises Galaxy. In yet other embodiments, the hops comprises Green Bullet. In yet other embodiments, the hops comprises Motueka. In yet other embodiments, the hops comprises Nelson Sauvin. In yet other embodiments, the hops comprises Pacific Gem. In yet other embodiments, the hops comprises Pacific Jade. In yet other embodiments, the hops comprises Pacifica. In yet other embodiments, the hops comprises Pride of Ringwood. In yet other embodiments, the hops comprises Riwaka. In yet other embodiments, the hops comprises Southern Cross. In yet other embodiments, the hops comprises Lublin. In yet other embodiments, the hops comprises Magnum. In yet other embodiments, the hops comprises Perle. In yet other embodiments, the hops comprises Polnischer Lublin. In yet other embodiments, the hops comprises Saphir. In yet other embodiments, the hops comprises Satus. In yet other embodiments, the hops comprises Select. In yet other embodiments, the hops comprises Strisselspalt. In yet other embodiments, the hops comprises Styrian Goldings. In yet other embodiments, the hops comprises Tardif de Bourgogne. In yet other embodiments, the hops comprises Tradition. In yet other embodiments, the hops comprises Bravo. In yet other embodiments, the hops comprises Calypso. In yet other embodiments, the hops comprises Chelan. In yet other embodiments, the hops comprises Comet. In yet other embodiments, the hops comprises El Dorado. In yet other embodiments, the hops comprises San Juan Ruby Red. In yet other embodiments, the hops comprises Satus. In yet other embodiments, the hops comprises Sonnet Golding. In yet other embodiments, the hops comprises Super Galena. In yet other embodiments, the hops comprises Tillicum. In yet other embodiments, the hops comprises Bramling Cross. In yet other embodiments, the hops comprises Pilgrim. Hallertauer Herkules. In yet other embodiments, the hops comprises Hallertauer Magnum. In yet other embodiments, the hops comprises Hallertauer Taurus. In yet other embodiments, the hops comprises Merkur. In yet other embodiments, the hops comprises Opal. In yet other embodiments, the hops comprises Smaragd. In yet other embodiments, the hops comprises Halleratau Aroma. In yet other embodiments, the hops comprises Kohatu. In yet other embodiments, the hops comprises Rakau. In yet other embodiments, the hops comprises Stella. In yet other embodiments, the hops comprises Sticklebract. In yet other embodiments, the hops comprises Summer Saaz. In yet other embodiments, the hops comprises Super Alpha. In yet other embodiments, the hops comprises Super Pride. In yet other embodiments, the hops comprises Topaz. In yet other embodiments, the hops comprises Wai-iti. In yet other embodiments, the hops comprises Bor. In yet other embodiments, the hops comprises Junga. In yet other embodiments, the hops comprises Marynka. In yet other embodiments, the hops comprises Premiant. In yet other embodiments, the hops comprises Sladek. In yet other embodiments, the hops comprises Styrian Atlas. In yet other embodiments, the hops comprises Styrian Aurora. In yet other embodiments, the hops comprises Styrian Bobek. In yet other embodiments, the hops comprises Styrian Celeia. In yet other embodiments, the hops comprises Sybilla. In yet other embodiments, the hops comprises Sorachi Ace.

BRIEF DESCRIPTION OF THE DRAWINGS

The following detailed description of specific embodiments of the invention will be better understood when read in conjunction with the appended drawings. For the purpose of illustrating the invention, the drawings illustrate specific embodiments. It should be understood, however, that the invention is not limited to the precise arrangements and instrumentalities of the embodiments shown in the drawings.

FIGS. 1A-1C are a non-limiting illustrative diagram outlining the methods used to select, isolate and characterize yeast strains of potential interest. Yeast strains of potential interest can be selected at step 102 where collected yeast strains are cultured with wort containing antibiotics and assessed for $CO_2$ production, wort density reduction, and tolerance for high dissolved sugar concentrations.

DETAILED DESCRIPTION OF THE INVENTION

Figure 1B:
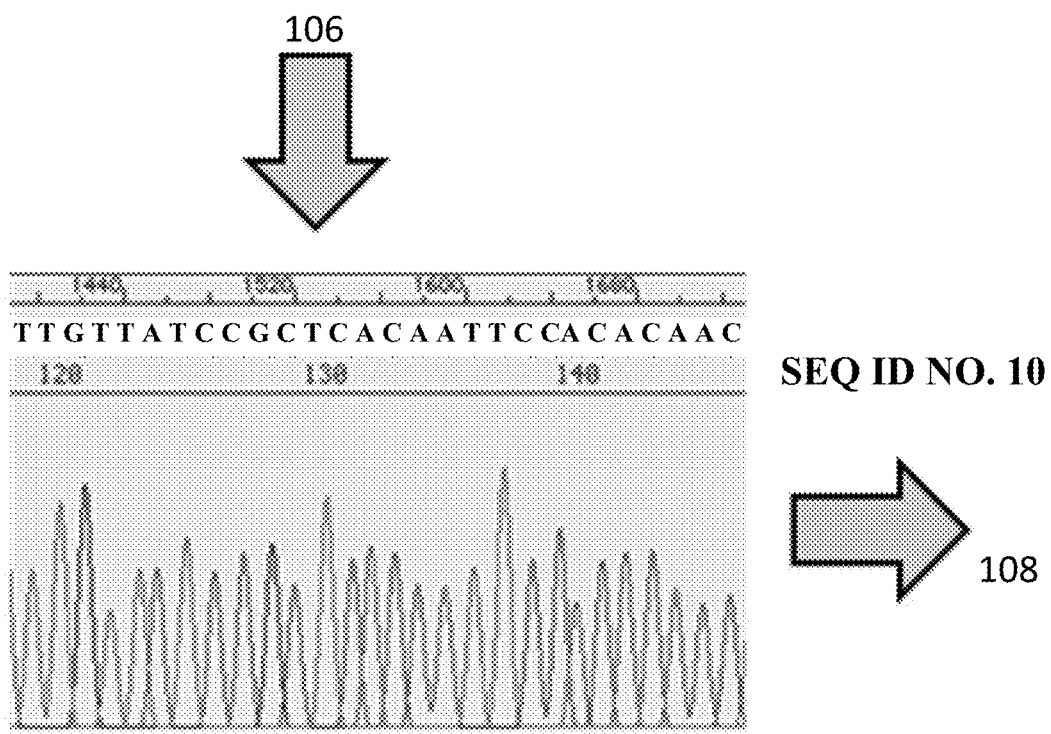

The present invention relates to the unexpected discovery of a new strain of yeast, dubbed GY7B, which is related to, but genetically and phenotypically distinct from, *Lachancea thermotolerans*. The invention provides methods of brewing a yeast-fermented beverage, such as but not limited to sour beer, using GY7B, wherein the methods do not require use of lactic acid and/or LAB. The methods of the invention can produce a wort with a pH of about 3.5 after fermenting for 5 days in the presence of GY7B, while methods known in the art using bacteria can take months to reach the same pH. In certain embodiments, the methods of the invention are performed without addition of lactic acid, or equivalents thereof, to the compositions contemplated within the invention. In other embodiments, within the methods of the invention, lactic acid, or any equivalents thereof, is not added during fermentation. In yet other embodiments, within the methods of the invention, lactic acid, or any equivalents thereof, is not added after fermentation. In yet other embodiments, the yeast contemplated within the invention is typically not of the *Lachancea thermotolerans* species.

Definitions

As used herein, each of the following terms has the meaning associated with it in this section.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

Generally, the nomenclature used herein and the laboratory procedures in yeast culturing and beer brewing are those well-known and commonly employed in the art.

As used herein, the articles "a" and "an" refer to one or to more than one (i.e., to at least one) of the grammatical object of the article. By way of example, "an element" means one element or more than one element.

As used herein, the term "about" is understood by persons of ordinary skill in the art and varies to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

As used herein, in certain embodiments the term "GY7B" may be referred to as the yeast deposited with the ATCC under Accession Number PTA-125167 on Jul. 19, 2018. In other embodiments, the GY7B yeast strain is characterized for having the nucleotide sequence of SEQ ID NO. 8 within the ITS region. In yet other embodiments, the GY7B yeast strain is characterized for having the nucleotide sequence of SEQ ID NO. 9 within the actin1 gene. In yet other embodiments, the GY7B yeast strain is characterized for having the nucleotide sequence of SEQ ID NO. 8 within the ITS region and the nucleotide sequence of SEQ ID NO. 9 within the actin1 gene.

"Instructional material," as that term is used herein, includes a publication, a recording, a diagram, or any other medium of expression that can be used to communicate the usefulness of the composition and/or compound of the invention in a kit. The instructional material of the kit may, for example, be affixed to a container that contains the compound and/or composition of the invention or be shipped together with a container that contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

As used herein, the term "low pH" in a fermented beverage indicates that the pH of the beverage is higher than or equal to about 2.5, and lower than or equal to about 4.5. The upper limit of low pH can be lower than or equal to about 4.5, lower than or equal to about 4.4, lower than or equal to about 4.3, lower than or equal to about 4.2, lower than or equal to about 4.1, and/or lower than or equal to about 4.0. The lower limit of the pH can be set as higher than or equal to about 2.5, higher than or equal to about 2.6, higher than or equal to about 2.7, higher than or equal to about 2.8, higher than or equal to about 2.9, higher than or equal to about 3.0, higher than or equal to about 3.1, higher than or equal to about 3.2, higher than or equal to about 3.3, higher than or equal to about 3.4, and/or higher than or equal to about 3.5. Any numerical ranges having the upper limits and the lower limits as shown elsewhere herein can be adopted. For example, the pH of the beverage can be in ranges of about 2.7 or higher, and about 4.5 or lower; about 2.7 or higher, and about 4.2 or lower; about 2.7 or higher, and about 4.0 or lower; about 3.0 or higher, and about 4.5 or lower; about 3.0 or higher, and about 4.2 or lower; about 3.1 or higher, and about 4.2 or lower; about 3.2 or higher, and about 4.2 or lower; about 3.3 or higher, and about 4.2 or lower; about 3.0 or higher, and about 4.0 or lower; about 3.5 or higher, and about 4.5 or lower; about 3.5 or higher, and about 4.2 or lower; and/or about 3.5 or higher, and about 4.0 or lower. In certain embodiments, the pH is about 2.5. In other embodiments, the pH is about 2.6. In yet other embodiments, the pH is about 2.7. In yet other embodiments, the pH is about 2.8. In yet other embodiments, the pH is about 2.9. In yet other embodiments, the pH is about 3.0. In yet other embodiments, the pH is about 3.1. In yet other embodiments, the pH is about 3.2. In yet other embodiments, the pH is about 3.3. In yet other embodiments, the pH is about 3.4. In yet other embodiments, the pH is about 3.5. In yet other embodiments, the pH is about 3.6. In yet other embodiments, the pH is about 3.7. In yet other embodiments, the pH is about 3.8. In yet other embodiments, the pH is about 3.9. In yet other embodiments, the pH is about 4.0. In yet other embodiments, the pH is about 4.1. In yet other embodiments, the pH is about 4.2. In yet other embodiments, the pH is about 4.3. In yet other embodiments, the pH is about 4.4. In yet other embodiments, the pH is about 4.5.

As used herein, the term "mash" is understood to mean a mix of milled grains and water used in brewing and distilling processes to produce wort. Typically malted grains are heated in order to breakdown the starch in the grains into simple sugars, which can then be fermented in order to produce alcohol.

As used herein, the "Plato scale" or "Plato gravity scale" refers to the empirically derived hydrometer scale used to measure the density of beer wort in terms of percentage of extract by weight. The terms "degrees Plato" or "° Plato" or "° P" are units of measurement on the Plato scale.

As used herein, the term "sour" in a fermented beverage refers to an acid, bitter, and/or sharp taste in the palate caused by the beverage. In certain embodiments, the sour taste is associated with the low pH of the fermented beverage.

As used herein, the term "wort" is understood to mean the liquid extracted from the mashing process during a brewing or distilling process. Wort contains the sugars extracted from the malted grains which will be fermented by the brewing yeast in order to produce alcohol.

Throughout this disclosure, various aspects of the invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The following abbreviations are used herein: BLAST, Basic local alignment search tool; DME, dry malt extract; IBU, International Bittering Units; LAB, lactic acid bacteria; nt, nucleotide; OD, Optical Density; PCR, polymerase chain reaction; P/S, Penicillin/Streptomycin; YPD, yeast extract peptone dextrose.

Compositions

The invention provides a yeast strain able to produce a yeast-fermented beverage with a low pH and a sour taste without the use of lactic acid producing bacteria. In other embodiments, the yeast strain is able to produce a yeast-fermented beverage with a pH of about 4.2 to about 3.3 without the use of lactic acid producing bacteria. In yet other embodiments, the yeast strain is able to reduce the pH of word to about 3.5 in about 5 days without the use of acid producing bacteria. In yet other embodiments, the yeast strain belongs to the genus *Lachancea*. In yet other embodiments, the yeast strain is GY7B (deposited with the ATCC under Accession Number PTA-125167 on Jul. 19, 2018). In yet other embodiments, the yeast strain comprises the nucleotide sequence of SEQ ID NO. 8 within the ITS region. In yet other embodiments, the yeast strain comprises the nucleotide sequence of SEQ ID NO. 9 within the actin1 gene. In yet other embodiments, the yeast strain comprises the nucleotide sequence of SEQ ID NO. 8 within the ITS region and the nucleotide sequence of SEQ ID NO. 9 within the actin1 gene.

In certain embodiments, the yeast strain of the invention is part of a composition. In other embodiments, the composition is compatible with fermentation processes. In yet other embodiments, the composition further comprises at least one additional yeast selected from the group consisting of *Saccharomyces, Lachancea,* and *Brettanomyces.* In yet other embodiments, the composition further comprises a *Saccharomyces* yeast. In yet other embodiments, the composition further comprises a distinct *Lachancea* yeast. In yet other embodiments, the composition further comprises a *Brettanomyces* yeast.

Methods

In one aspect, the present invention provides a method of producing a yeast fermented beverage with a low pH and sour taste without the use of lactic acid producing bacteria.

In certain embodiments, the invention provides a method of producing a yeast-fermented beverage. In other embodiments, the method comprises fermenting a wort in the presence of a yeast strain able to produce a yeast-fermented beverage with a low pH and a sour taste without the use of lactic acid producing bacteria. In certain embodiments, the yeast-fermented beverage is beer.

In certain embodiments, the method does not comprise use of lactic acid, or any equivalent thereof. In other embodiments, lactic acid, or any equivalent thereof, is not added to the wort, before, during, or after fermentation.

In certain embodiments, the yeast strain is able to produce a yeast-fermented beverage with a pH of about 4.2 to about 3.3 without the use of lactic acid producing bacteria. In other embodiments, the yeast strain is able to reduce the pH of wort to about 3.5 in about 5 days without the use of acid producing bacteria. In yet other embodiments, the yeast strain belongs to the genus *Lachancea.* In yet other embodiments, the yeast strain is GY7B (deposited with the ATCC under Accession Number PTA-125167 on Jul. 19, 2018). In yet other embodiments, the yeast strain comprises the nucleotide sequence of SEQ ID NO. 8 within the ITS region. In yet other embodiments, the yeast strain comprises the nucleotide sequence of SEQ ID NO. 9 within the actin1 gene. In yet other embodiments, the yeast strain comprises the nucleotide sequence of SEQ ID NO. 8 within the ITS region and the nucleotide sequence of SEQ ID NO. 9 within the actin1 gene.

In certain embodiments, the method produces a yeast-fermented beverage with a pH of about 4.2 to about 3.3. In other embodiments, the wort is fermented in the absence of any acid producing bacteria. In yet other embodiments, the wort is fermented in the absence of any lactic acid producing bacteria. In yet other embodiments, the wort is fermented in the absence of bacteria belonging to genera *Lactobacillus* or *Pediococcus.* In yet other embodiments, the wort comprises malt derived from one or more grains selected from the group consisting of barley, wheat, corn, rye, rice, oats, sorghum, millet, buckwheat, quinoa, and teff. In yet other embodiments, the wort further comprises hops. In yet other embodiments, the wort is fermented in the presence of at least one additional yeast strain selected from the group consisting of *Saccharomyces cerevisiae, Saccharomyces pastorianus, Saccharomyces paradoxus, Saccharomyces eubayanus, Saccharomyces ludwigii, Aureobasidium pullulans, Cyberlindnera saturnus, Hansensiaspora uvarum, Hansensiaspora guilliermondii, Hansensiaspora osmophila, Hansensiasporavineae, Hansenula anomala, Issatchenkia occidentalis, Issatchenkia orientalis, Pichia kluyveri, Pichia caribbica, Pichia fermentans, Pichia kudriavzevii, Pichia Membranifaciens, Rhodotorula mucilaginosa, Torulaspora delbrueckii, Candida colliculosa, Candida shehatae, Candida tropicalis, Candida ethanolica, Candida krusei, Candida magnolia, Candida milleri, Clavispora lusitaniae, Wickerhamomyces subpelliculosus, Wickerhamomyces anomalus, Zygosaccharomyces rouxii, Zygosaccharomyces bailii, Zygosaccharomyces fermentati, Zygosaccharomycesflorentinus, Kluyveromyces lactis, Kluyveromyces marxianus, Lachancea thermotolerans, Brettanomyces bruxellensis, Brettanomyces anomalus, Brettanomyces custersianus, Brettanomyces naardenensis, Brettanomyces nanus, Dekkera bruxellensis,* and *Dekkera anomala.*

In certain embodiments, the hops is at least one selected from the group consisting of Ahtanum, Amarillo, Apollo, Cascade, Centennial, Chinook, Citra, Cluster, Columbus, Crystal, Eroica, Galena, Glacier, Greenburg, Horizon, Liberty, Millenium, Mount Hood, Mount Rainier, Newport, Nugget, Palisade, Santiam, Simcoe, Sterling, Summit, Tomahawk, Ultra, Vanguard, Warrior, Willamette, Zeus, Admiral, Brewer's Gold, Bullion, Challenger, First Gold, Fuggles, Goldings, Herald, Northdown, Northern Brewer, Phoenix, Pilot, Pioneer, Progress, Target, Whitbread Golding Variety (WGV), Hallertau, Hersbrucker, Saaz, Tettnang, Spalt, Feux-Coeur Francais, Galaxy, Green Bullet, Motueka, Nelson Sauvin, Pacific Gem, Pacific Jade, Pacifica, Pride of Ringwood, Riwaka, Southern Cross, Lublin, Magnum, Perle, Polnischer Lublin, Saphir, Satus, Select, Strisselspalt, Styrian Goldings, Tardif de Bourgogne, Tradition, Bravo, Calypso, Chelan, Comet, El Dorado, San Juan Ruby Red, Satus, Sonnet Golding, Super Galena, Tillicum, Bramling Cross, Pilgrim. Hallertauer Herkules, Hallertauer Magnum, Hallertauer Taurus, Merkur, Opal, Smaragd, Halleratau Aroma, Kohatu, Rakau, Stella, Sticklebract, Summer Saaz, Super Alpha, Super Pride, Topaz, Wai-iti, Bor, Junga, Marynka, Premiant, Sladek, Styrian Atlas, Styrian Aurora, Styrian Bobek, Styrian Celeia, Sybilla, and Sorachi Ace.

The invention further provides use of a yeast strain contemplated herein, and/or a kit contemplated herein, to produce a beer with a low pH and a sour taste. In certain embodiments, the beer is produced without the use of lactic acid producing bacteria. In other embodiments, the beer is produced without the use of lactic acid. In yet other embodiments, the beer has a pH of about 4.2 to about 3.3.

In certain embodiments, the method comprises fermenting wort in the presence of GY7B yeast. In certain embodiments, the method produces the sour tasting yeast fermented beverage faster than known methods that use lactic acid producing bacteria.

In certain embodiments, the yeast fermented beverage is a beer. In other embodiments, beer is a sour beer similar in style to a beer selected from the group consisting of lambic, geuze (gueuze), saison, farmhouse, framboise, kriek, Berliner weisse, Flanders red ale, oud bruin, gose and American wild ale.

In certain embodiments, the GY7B yeast reduces the pH of wort to about 3.5 in about 5 days without the use of acid producing bacteria. In other embodiments, the GY7B yeast is more tolerant to low pH than common brewers yeasts known in the art, such as but not limited to *Saccharomyces cerevisiae* and *Lachancea thermotolerans.* In other embodiments, the GY7B yeast thrives in environments as low as pH 3. In yet other embodiments, the GY7B yeast produces a beer with a pH of about 4.2 to about 3.3.

In certain embodiments, the GY7B yeast tolerates alcohol concentrations up to about 10% vol/vol alcohol.

The process of brewing beer is well known to the skilled person and may be outlined in the following non-limiting way. Malt can be prepared from dried, germinated cereal grains (mainly barley or wheat) and grounded into a grist that may contain unmalted adjuncts. The grist can be mashed (mixed with water and steeped) to allow enzymes in the malt to convert the starch into sugars. The grain particles and adjuncts can be separated from the liquid wort in a process called lautering. The malt making and mashing steps can be skipped by adding water to malt extract. After addition of hops and/or other ingredients such as herbs and sugars, the wort can be boiled (hops may also be added after boiling), cooled and aerated. The wort can then be moved to a fermentation tank and fermented by the addition of a brewer's yeast. The primary fermentation, lasting typically 5 to 10 days, may be followed by a secondary fermentation step using a further brewer's yeast. After fermentation the fresh beer or "green" beer, can be conditioned, optionally filtrated and carbonated.

Hops are added to the wort to balance the sweetness of the malt with bitterness and impart onto the beer desirable flavors and aromas. Several varieties exist, including but not limited, to Ahtanum, Amarillo, Apollo, Cascade, Centennial, Chinook, Citra, Cluster, Columbus, Crystal, Eroica, Galena, Glacier, Greenburg, Horizon, Liberty, Millenium, Mount Hood, Mount Rainier, Newport, Nugget, Palisade, Santiam, Simcoe, Sterling, Summit, Tomahawk, Ultra, Vanguard, Warrior, Willamette, Zeus, Admiral, Brewer's Gold, Bullion, Challenger, First Gold, Fuggles, Goldings, Herald, Northdown, Northern Brewer, Phoenix, Pilot, Pioneer, Progress, Target, Whitbread Golding Variety (WGV), Hallertau, Hersbrucker, Saaz, Tettnang, Spalt, Feux-Coeur Francais, Galaxy, Green Bullet, Motueka, Nelson Sauvin, Pacific Gem, Pacific Jade, Pacifica, Pride of Ringwood, Riwaka, Southern Cross, Lublin, Magnum, Perle, Polnischer Lublin, Saphir, Satus, Select, Strisselspalt, Styrian Goldings, Tardif de Bourgogne, and Tradition. Further varieties exist, including but not limited to, Bravo, Calypso, Chelan, Comet, El Dorado, San Juan Ruby Red, Satus, Sonnet Golding, Super Galena, Tillicum, Bramling Cross, Pilgrim, Hallertauer Herkules, Hallertauer Magnum, Hallertauer Taurus, Merkur, Opal, Smaragd, Halleratau Aroma, Kohatu, Rakau, Stella, Sticklebract, Summer Saaz, Super Alpha, Super Pride, Topaz, Wai-iti, Bor, Junga, Marynka, Premiant, Sladek, Styrian Atlas, Styrian Aurora, Styrian Bobek, Styrian Celeia, Sybilla, and Sorachi Ace.

In certain embodiments, the yeast fermented beverage is produced by fermenting wort derived from a mash comprising one or more grains selected from the group consisting of barley, wheat, corn, rye, nice, oats, sorghum, millet, buckwheat, quinoa, teff, dry malt extract, and liquid malt extract. In certain embodiments, the yeast fermented beverage may contain additional fermentable sugar as provided by adjuncts such as, but not limited to purified sugars or syrups. In certain embodiments, the mash comprises malted grains. In certain embodiments, the method further comprises the addition of flowers of the hop plant ("hops"), *Humulus lupulus*, to the wort. In certain embodiments, the hops are added to the wort before addition of the GY7B yeast. In certain embodiments, the hops are added to the fermenting beer after addition of the GY7B yeast.

In certain embodiments, the method comprises fermenting wort in the presence of GY7B yeast alone or in the presence of at least one additional yeast strain selected from the group consisting of *Saccharomyces cerevisiae, Saccharomyces pastorianus, Saccharomyces paradoxus, Saccharomyces eubayanus, Saccharomyces ludwigii, Aureobasidium pullulans, Cyberlindnera saturnus Hansensiaspora uvarum Hansensiaspora guilliermondii, Hansensiaspora osmophila, Hansensiasporavineae, Hansenula anomala, Issatchenkia occidentalis, Issatchenkia orientalis, Pichia kluyveri, Pichia caribbica, Pichia fermentans, Pichia kudriavzevii, Pichia Membranifaciens, Rhodotorula mucilaginosa, Torulaspora delbrueckii, Candida colliculosa, Candida shehatae, Candida tropicalis, Candida ethanolica, Candida krusei, Candida magnolia, Candida milleri, Clavispora lusitaniae Wickerhamomyces subpelliculosus, Wickerhamomyces anomalus, Zygosaccharomyces rouxii, Zygosaccharomyces bailii, Zygosaccharomyces fermentati, Zygosaccharomycesflorentinus, Kluyveromyces lactis, Kluyveromyces marxianus, Lachancea thermotolerans, Brettanomyces bruxellensis, Brettanomyces anomalus, Brettanomyces custersianus, Brettanomyces naardenensis, Brettanomyces nanus, Dekkera bruxellensis* and *Dekkera anomala.*

In certain embodiments, the starting gravity of the wort is from about 6° P to about 25° P. In other embodiments, the starting gravity of the wort is about 10° P to about 16° P.

In certain embodiments, the concentration of GY7B in the wort is about $1 \times 10^6$ cells/mL to about $2 \times 10^7$ cells/ml.

In certain embodiments, the wort is fermented at a temperature of about 9° C. to about 30° C. In other embodiments, the wort is fermented at about 20° C.

In certain embodiments, the method requires minimal, or no, filtering. GY7B demonstrates high flocculation and rapidly settles to the bottom of the fermenting vessel, easing separation. In certain embodiments, the method facilitates flocculation of additional yeast strains during co-fermentation.

In certain embodiments, the method further comprises pasteurization. In other embodiments, the fermented wort is pasteurized at 15-30 Pasteurization Units.

In certain embodiments, the GY7B is added to the fermenter. In other embodiments, GY7B is added to the mash. In other embodiments, GY7B is added to a secondary fermentation or maturation vessel such as a fermenter, barrel, foeder, bright tank, keg, cask, can, or bottle.

Kits

The invention provides a kit comprising at least one yeast strain contemplated herein and one or more items or ingredients suitable to produce a yeast-fermented beverage. The invention further provides a kit comprising yeast strain GY7B (deposited with the ATCC under Accession Number PTA-125167 on Jul. 19, 2018), and one or more items or ingredients suitable to produce a yeast-fermented beverage. The invention further provides a kit comprising a yeast strain from the genus *Lachancea*, wherein the yeast strain comprises the nucleotide sequence of SEQ ID NO. 8 within the ITS region and/or the nucleotide sequence of SEQ ID NO. 9 within the actin1 gene, and one or more items or ingredients suitable to produce a yeast-fermented beverage.

In certain embodiments, the kit further comprises instructional materials comprising instructions for producing a yeast-fermented beverage using the yeast strain contemplated.

In certain embodiments, the yeast-fermented beverage is beer.

In certain embodiments, the one or more items or ingredients comprise at least one item selected from the group consisting of: prepared wort solution; dry malt extract; one or more grains selected from the group consisting of barley, wheat, corn, rye, rice, oats, sorghum, millet, buckwheat, quinoa, and teff; at least one additional yeast strain selected from the group consisting of *Saccharomyces cerevisiae, Saccharomyces pastorianus, Saccharomyces paradoxus, Saccharomyces eubayanus, Saccharomyces ludwigii, Aureobasidium pullulans, Cyberlindnera saturnus, Hansensiaspora uvarum, Hansensiaspora guilliermondii, Hansensiaspora osmophila, Hansensiasporavineae, Hansenula*

*anomala, Issatchenkia occidentalis, Issatchenkia orientalis, Pichia kluyveri, Pichia caribbica, Pichia fermentans, Pichia kudriavzevii, Pichia Membranifaciens, Rhodotorula mucilaginosa, Torulaspora delbrueckii, Candida colliculosa, Candida shehatae, Candida tropicalis, Candida ethanolica, Candida krusei, Candida magnolia, Candida milleri, Clavispora lusitaniae, Wickerhamomyces subpelliculosus, Wickerhamomyces anomalus, Zygosaccharomyces rouxii, Zygosaccharomyces bailii, Zygosaccharomyces fermentati, Zygosaccharomycesflorentinus, Kluyveromyces lactis, Kluyveromyces marxianus, Lachancea thermotolerans, Brettanomyces bruxellensis, Brettanomyces anomalus, Brettanomyces custersianus, Brettanomyces naardenensis, Brettanomyces nanus, Dekkera bruxellensis,* and *Dekkera anomala*; one or more varieties of hops; conditioned brewing water; and one or more sugar adjuncts. Illustrative examples of hops contemplated are described elsewhere herein.

The invention further provides kits comprising GY7B and items and ingredients necessary to brew beer.

In certain embodiments, the kit comprises packaged GY7B. In other embodiments, the kit comprises dried GY7B in the form of a powder. In other embodiments, the kit comprises GY7B in a vacuum sealed container. In other embodiments, the kit comprises GY7B from a fresh propagation or a post-fermentation slurry in a vented container.

In certain embodiments, the kit further comprises one or more items necessary for performing the methods of the invention selected from the group consisting of one or more vessels adapted and configured for wort fermentation, one or more thermometers, one or more hydrometers, one or more vessels adapted and configured for wort boiling, one or more vessels adapted and configured for pasteurization, one or more vessels adapted and configured for beer storage, one more vessels adapted and configured for aging of beer. In other embodiments, the kit further comprises one or more items selected from the group consisting of compressed $CO_2$ tanks, compressed $N_2$ tanks, gas regulators, tubing, and pressure gauges.

In certain embodiments, the kit further comprises at least one additional ingredient necessary for performing the methods of the invention selected from the group consisting of prepared wort solution, dry or liquid malt extract, one or more grains selected from the group consisting of barley, wheat, corn, rye, rice, oats, sorghum, millet, buckwheat, quinoa, and teff, at least one additional yeast strain selected from the group consisting of *Saccharomyces cerevisiae, Saccharomyces pastorianus, Saccharomyces paradoxus, Saccharomyces eubayanus, Saccharomyces ludwigii, Aureobasidium pullulans, Cyberlindnera saturnus Hansensiaspora uvarum Hansensiaspora guilliermondii, Hansensiaspora osmophila, Hansensiasporavineae, Hansenula anomala, Issatchenkia occidentalis, Issatchenkia orientalis, Pichia kluyveri, Pichia caribbica, Pichia fermentans, Pichia kudriavzevii, Pichia Membranifaciens, Rhodotorula mucilaginosa, Torulaspora delbrueckii, Candida colliculosa, Candida shehatae, Candida tropicalis, Candida ethanolica, Candida krusei, Candida magnolia, Candida milleri, Clavispora lusitaniae Wickerhamomyces subpelliculosus, Wickerhamomyces anomalus, Zygosaccharomyces rouxii, Zygosaccharomyces bailii, Zygosaccharomyces fermentati, Zygosaccharomycesflorentinus, Kluyveromyces lactis, Kluyveromyces marxianus, Lachancea thermotolerans, Brettanomyces bruxellensis, Brettanomyces anomalus, Brettanomyces custersianus, Brettanomyces naardenensis, Brettanomyces nanus, Dekkera bruxellensis,* and *Dekkera anomala,* one or more varieties of hops, conditioned brewing water, and one or more sugar adjuncts.

In certain embodiments, the kit further comprises instructional materials containing instructions for performing the methods of the invention. In certain embodiments, the instructional materials provide information pertaining to brewing beer with GY7B using the items and ingredients of the kit of the invention.

An exemplary yeast strain of the invention is the GY7B yeast strain. Under the terms of the Budapest Treaty on the International Recognition of the Deposit of Microorganisms for the Purpose of Patent Procedure, deposit of the yeast strain was made with the American Type Culture Collection (ATCC) of Rockville, Md., USA.

Applicant's assignee, University of the Sciences, represents that the ATCC is a depository afforded permanence of the deposit and ready accessibility thereto by the public if a patent is granted. All restrictions on the availability to the public of the material so deposited will be irrevocably removed upon granting of a patent. The material will be readily available during the pendency of the patent application to one determined by the Commissioner to be entitled thereto under 37 C.F.R. § 1.14 and 35 U.S.C. § 122. The deposited material will be maintained with all the care necessary to keep it viable and uncontaminated for a period of at least five years after the most recent request for the furnishing of a sample of the deposited material, and in any case, for a period of at least thirty (30) years after the date of the deposit or for the enforceable life of the patent, whichever period is longer. Applicants' assignee acknowledges its duty to replace the deposit should the depository be unable to furnish a sample when requested due to the condition of the deposit.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, with art-recognized alternatives and using no more than routine experimentation, are within the scope of the present application.

It is to be understood that, wherever values and ranges are provided herein, the description in range format is merely for convenience and brevity and should not be construed as an inflexible limitation on the scope of the invention. Accordingly, all values and ranges encompassed by these values and ranges are meant to be encompassed within the scope of the present invention. Moreover, all values that fall within these ranges, as well as the upper or lower limits of a range of values, are also contemplated by the present application. The description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials and Methods

Sample Collection Methods

Samples for wild yeast isolation were collected using aseptic technique in the field. Samples were then inoculated directly in a 10% DME (BREISS®) solution containing Penicillin/Streptomycin (P/S) (GIBCO®). After two weeks, samples were plated on YPD containing P/S and cultured at 25° C. for 48 hours. Individual colonies were selected for further propagation on YPD P/S plates under the same culture conditions. Purity of colonies was validated by uniformity in morphology, at which point colonies were maintained on YPD plates without antibiotics. Glycerol stocks were created by picking a colony and culturing in YPD broth at 25° C., 180 rpm for 48 hours. Then cultures were then incubated at 4° C. for another 48 hours. Finally, the yeast were resuspended in fresh YPD with 15% glycerol and frozen in cryovials at −80° C. All experiments were run with yeast freshly propagated from glycerol stocks.

Test Ferment Wort Formulation

Test fermentations were either performed in 10% DME, unhoped media, referred to as laboratory wort or in wort prepared in the University of the Sciences pilot brewery. For 10% DME laboratory wort, 100 g of DME was dissolved in 1 L of distilled water, boiled for 15 minutes, and cooled to room temperature. 10° P wort was prepared in the USciences pilot brewery using 100% 2-row pale malt (BREISS®). It was milled and mashed on a SABCO™ BrewMagic using distilled water at 65° C. for 60 min. After vorlauf, continuous fly sparging was performed with 75° C. distilled water acidified to pH6.0 with food-grade lactic acid (SPECTRUM® chemicals). The wort was boiled for 60 minutes, with a 60 minute bittering addition of 007: The Golden Hop (Yakima Valley Hops) to yield 10IBU of bitterness. Whirlfloc (LD CARLSON™) was added with 15 min remaining in the boil as per the manufacturer's instructions. The yeast supplement Servomyces (WHITE LABS) was added with 10 min remaining in the boil as per the manufacturer's instructions. After the boil, the wort was brought into a whirlpool and allowed to settle for 15 min before chilling to room temperature with the SABCO Chill Wizard. All wort was bottled, autoclaved and stored at 4° C. before use.

Yeast Culture Plates

YPD agar (2% glucose, 2% peptone, 1% yeast extract, and 1.5% agar) was supplemented with a 1:100 dilution of P/S as needed. All reagents were from Research Products International.

Yeast Strains

The following strains were used for comparison to GY7B: Wyeast American Ale II, *Saccharomyces cerevisiae* (Wy 1272); Lallemand Belle Saison, *Saccharomyces cerevisiae*; NRRL Y-8284/CBS6340$^T$, *Lachancea thermotolerans*

PCR for Yeast Identification

For yeast identification, fresh yeast cultures grown at 25-30° C. for <48 hours on YPD were used. Crude DNA extraction was performed by selecting a small yeast colony and transferring to 0.2% SDS followed by incubation at 90° C. for 4 minutes. The lysed yeast were then diluted 1:10 in nuclease-free water. This dilution was further diluted 1:40 into the PCR reaction. PCR was performed with Phusion High-fidelity PCR kit (NEW ENGLAND BIOLABS®) as per the manufacturer's instructions on an EPPENDORF® Mastercycler. The D1/D2 domain of the 26S rDNA region was amplified using the primers NL1 (SEQ ID NO. 1: 5'-GCATATCAATAAGCGGAGGAAAAG-3') and NL4 (SEQ ID NO. 2: 5'-GGTCCGTGTTTCAAGACGG-3'). Amplification was performed for 36 cycles with denaturation at 98° C. for 10 sec, annealing at 52° C. for 20 sec, and extension at 72° C. for 20 sec.

The ITS region of the rDNA was amplified using primers ITS1 (SEQ ID NO. 3: 5'-TCCGTAGGTGAACCTGCGG-3') and ITF4 (SEQ ID NO. 4: 5'-TCCTCCGCTTATTGA-TATGC-3'). Amplification was performed using 34 cycles with denaturation at 98° C. for 10 sec, annealing at 50° C. for 20 sec with a 0.2° C. increase each cycle, and extension at 72° C. for 20 sec. The actin1 gene was amplified using primers CA21 (SEQ ID NO. 5: 5'-ATTGA-TAACGGTTCCGGTATGTG-3') and CA22R (SEQ ID NO. 6: 5'-TCGTCGTATTCTTGCTTTGAGATCCAC-3'). Amplification was performed using 20 cycles with denaturation at 98° C. for 10 sec, annealing at 60° C. for 30 sec with a 0.5° C. decrease each cycle, and extension at 72° C. for 30 sec followed by 15 cycles with denaturation at 98° C. for 10 sec, annealing at 50° C. for 30 sec, and extension at 72° C. for 30 sec.

Gel Electrophoresis and Purification

PCR reactions were resolved on a 1% agarose gel at 120 volts (BIO-RAD®) and visualized with ethidium bromide under UV light. Bands were excised and purified using the GeneJet Gel Extraction kit (THERMO FISHER SCIENTIFIC®) according to manufacturer's instructions.

Sequencing Analysis

Purified PCR DNA was prepared for Sanger sequencing by Genewiz according to their instructions. Each PCR product was sequenced with both the forward and the reverse primers used in the original PCR amplification. Returned sequences were validated for accuracy by aligning the forward and the reverse sequences with A Plasmid Editor (M. Wayne Davis). Any discrepancies were further resolved by visual analysis of the chromatogram. Any sequence lacking double coverage was discarded. Validated sequences were analyzed with Nucleotide BLAST (NCBI) using default parameters.

Example 1: Methods of Collecting and Testing Wild Yeast Strains

Referring to FIGS. 1A-1C, samples were collected from Woodlands Cemetery (4000 Woodland Ave, Philadelphia, PA 19104) from local flowering trees, as well as a local bee hive by swabbing (101) and inoculating in sterile wort (102). The samples were incubated without shaking at 25° C. for about 1 week. Sediment was gently re-suspended and plated onto YPD plates (103). Once visible colonies were present after 48-72 hr growth at 25° C., morphologically distinct colonies were sub-cultured to purity (104). The purified yeast strains were subject to PCR of the D1/D2 region to amplify the genetic material for analysis (105). The extracted DNA was separated through gel electrophoresis (106), sequenced (107), and analyzed using the Basic Local Alignment Search Tool (BLAST) to find genetic similarities (108). Table 1A lists all strains isolated and their source. Table 1B lists the similarity between the yeast isolate's D1/D2 sequence and the top BLAST hit. In addition, test ferments containing laboratory wort were inoculated with the isolated yeast and observed for a period of 7 days. Of the samples collected GY7B was the most robust fermenter as demonstrated by visible $CO_2$ evolution in the sample tube.

GY7B was isolated from a *Cornecaea cornus* (Dogwood tree) bud. BLAST analysis of the D1/D2 sequence returned a 1000 match with 0 nt differences to *Lachancea thermotolerans*, indicating it is a wild strain related to *L. thermotolerans*.

TABLE 1A

Identification of Wild Yeast Strains by D1/D2 sequencing

| Sample ID | Phylum | Order | Source |
|---|---|---|---|
| GG1.1.1 | Basidiomycota | Filobasidiales | Corvallis |
| GG1.1.2 | Ascomycota | Sporidiales | Corvallis |
| GG1.1.4 | Ascomycota | Dothideales | Corvallis |
| GG1.1.5 | Basidiomycota | Tremellales | Corvallis |
| PF1.1.1 | Ascomycota | Dothideales | Nyctaginaceae |
| PF1.1.2 | Ascomycota | Dothideales | Nyctaginaceae |
| PF1.1.3 | Basidiomycota | Sporidiobolales | Nyctaginaceae |
| PF1.1.4 | Ascomycota | Sporidiales | Nyctaginaceae |
| RF1.1.1 | Basidiomycota | Tremellales | Camellia japonica |
| RB1.3.1 | Basidiomycota | Sporidiobolales | Corvallis |
| PF1.2.3 | Ascomycota | Dothideales | Nyctaginaceae |
| RF1.2.2 | Basidiomycota | Tremellales | Camellia japonica |
| PF1.2.2 | Ascomycota | Dothideales | Nyctaginaceae |
| PF1.2.1 | Ascomycota | Sporidiales | Nyctaginaceae |
| GG1.1.3 | Basidiomycota | Sporidiobolales | Corvallis |
| RB1.2.1 | Ascomycota | Saccharomycetales | Corvallis |
| GY7.1 | Ascomycota | Saccharomycetales | Cornaceae cornus |
| GY7.2 | Ascomycota | Saccharomycetales | Cornaceae cornus |
| GY4.1 | Ascomycota | Saccharomycetales | Bee Hive |
| GY6.1 | Ascomycota | Saccharomycetales | Hedera |
| GY9.1 | Ascomycota | Saccharomycetales | Hedera |

TABLE 1B

Identification of Wild Yeast Strains by D1/D2 sequencing

| Sample ID | Base Pairs | Top BLAST Hit | % ID | nt diff. |
|---|---|---|---|---|
| GG1.1.1 | 546 | *Filobasidium elegans* | 100 | 0 |
| GG1.1.2 | 480 | *Rhodosporidium fluviale* | 99 | 1 |
| GG1.1.4 | 554 | *Aureobasidium pullulans* | 99 | 1 |
| GG1.1.5 | 546 | *Cryptococcus magnus* | 100 | 0 |
| PF1.1.1 | 557 | *Aureobasidium pullulans* | 99 | 1 |
| PF1.1.2 | 684 | *Aureobasidium pullulans* | 100 | 0 |
| PF1.1.3 | 517 | *Sporidiobulus ruineniae* | 100 | 0 |
| PF1.1.4 | 517 | *Rhodosporidium babjevae* | 100 | 0 |
| RF1.1.1 | 530 | *Cryptococcus* sp. | 100 | 0 |
| RB1.3.1 | 534 | *Rhodotorula* sp. | 100 | 0 |
| PF1.2.3 | 511 | *Aureobasidium pullulans* | 100 | 0 |
| RF1.2.2 | 529 | *Cryptococcus* sp. | 100 | 0 |
| PF1.2.2 | 499 | *Aureobasidium pullulans* | 100 | 0 |
| PF1.2.1 | 512 | *Rhodosporidium babjevae* | 100 | 0 |
| GG1.1.3 | 526 | *Rhodotorula hinnulea* | 100 | 0 |
| RB1.2.1 | 555 | *Candida parapsilosis* | 100 | 0 |
| GY7.1 | 528 | *Hanseniaspora uvarum* | 99 | 2 |
| GY7B | 540 | *Lachancea thermotolerans* | 100 | 0 |
| GY4.1 | 553 | *Pichia kudriavzevii* | 100 | 0 |
| GY6.1 | 553 | *Pichia kudriavzevii* | 100 | 0 |
| GY9.1 | 553 | *Pichia kudriavzevii* | 100 | 0 |

Example 2: Fermentation Trials Using GY7B

Figure 2A:
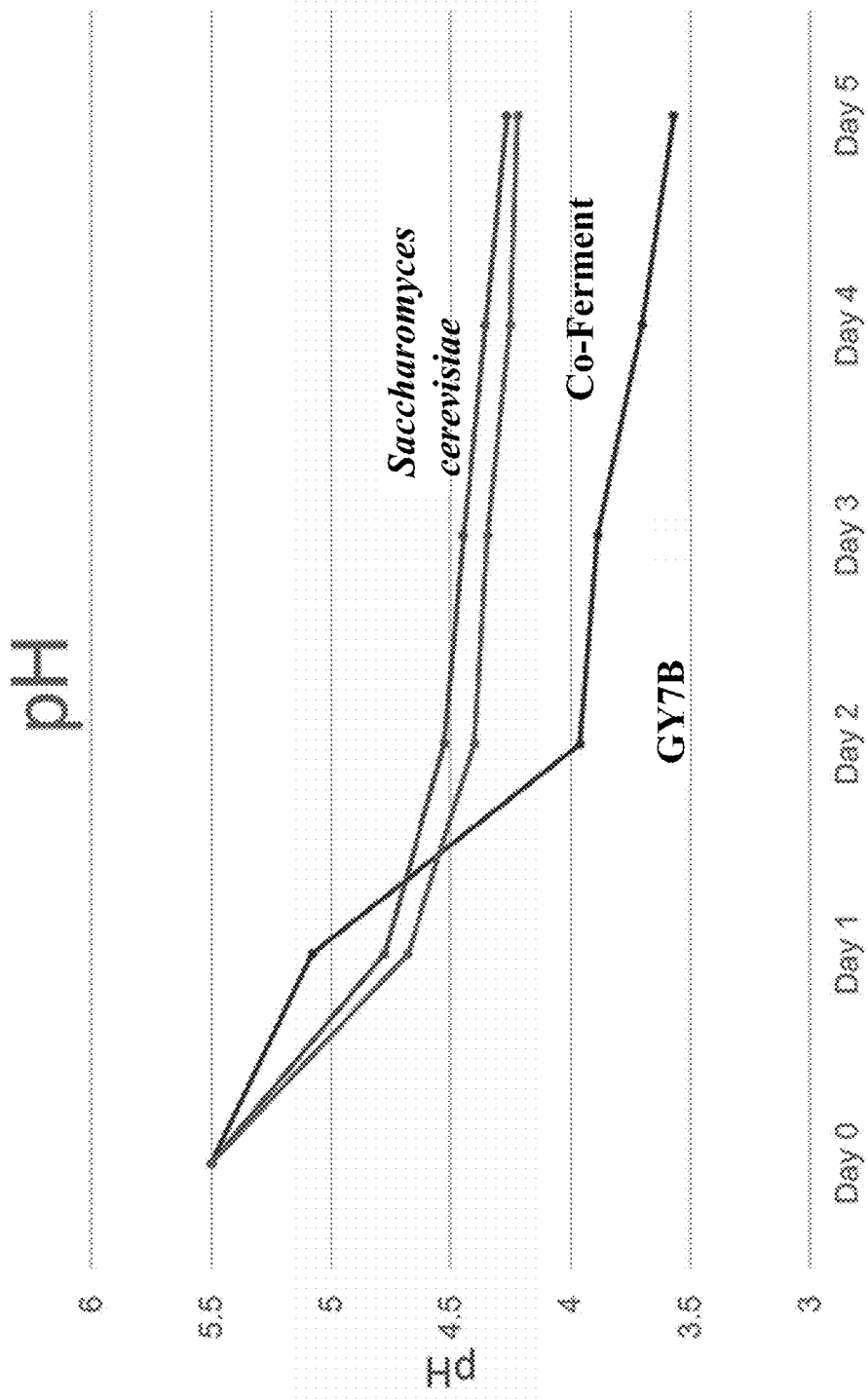
FIGS. 2A-2B are graphs reporting pH (FIG. 2A) and apparent extract (FIG. 2B) of fermentation trials of 10% light dry malt extract (DME) unhoped wort using *Saccharomyces cerevisiae* (*Belle Saison* strain; Lallemand), a newly discovered yeast strain GY7B, and a mixture of both strains. The wort was incubated at 20° C. and inoculated with $1 \times 10^6$ yeast cells per milliliter per degree Plato. The GY7B strain demonstrated greater acidification and a greater longevity than the *Saccharomyces cerevisiae* or the mixed strain samples. As demonstrated in FIG. 2B, GY7B does not ferment as quickly as the *Saccharomyces cerevisiae* strain used in this trial. Without being limited to any one theory, it is possible that the lack of acidification observed in co-fermentation between GY7B and *Saccharomyces cerevisiae* is due to the faster fermentation abilities of traditional ale yeast strains that outcompetes GY7B's ability to create lactic acid.

Once identified, isolated GY7B was tested for wort fermentation under controlled conditions. Laboratory wort was inoculated with $1\times10^6$ yeast cells/ml/° P of *Saccharomyces cerevisiae* (strain *Belle Saison* from Lallemand), GY7B, or both strains each at $1\times10^6$ yeast cells/ml/° P. The ferments were incubated at 20° C. for 5 days. The pH and apparent extract of the ferments were tracked daily using a pH meter and a densitometer, respectively. GY7B reduced the pH of the wort to about 3.5 after 5 days, while both the *S. cerevisiae* and mixed strain samples reduced the pH of the wort to only about 4.25 after 5 days (FIG. 2A).

Figure 2B:
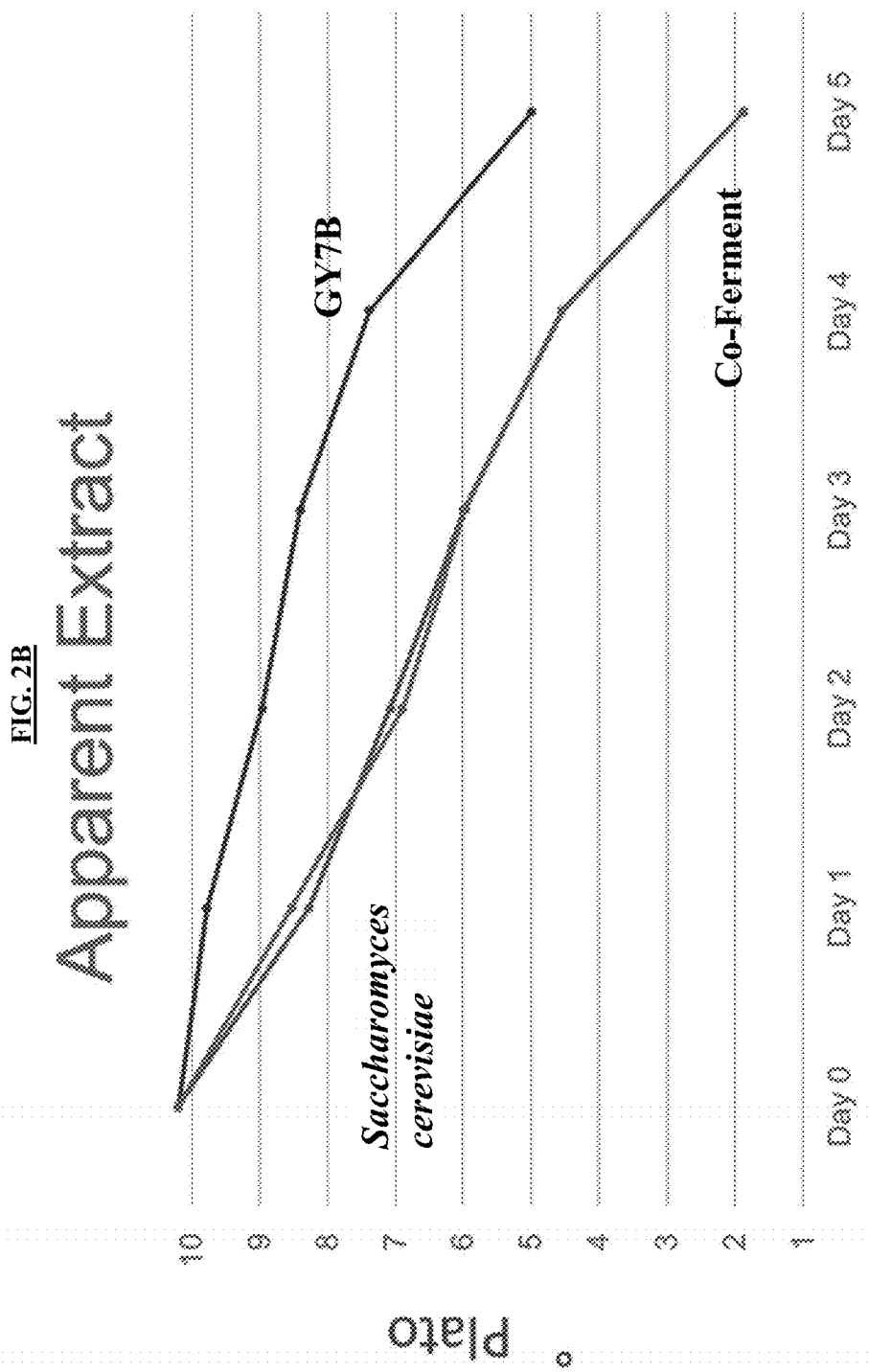

GY7B was found to be a slower fermenting yeast than *S. cerevisiae*, as both the *S. cerevisiae* and mixed strain samples demonstrated a faster decrease in ° P over 5 days than the GY7B sample (FIG. 2B). Without being limited to any particular theory, it is suspected that the lack of acidification observed in co-fermentation between GY7B and *Saccharomyces cerevisiae* is due to the faster fermentation abilities of *S. cerevisiae* which outcompetes GY7B's ability to create lactic acid. Optimization of cell inoculation rates during co-fermentation allows the timely production of sour beer via GY7B with the benefits of fermentation with a traditional ale strain.

Figure 2C:
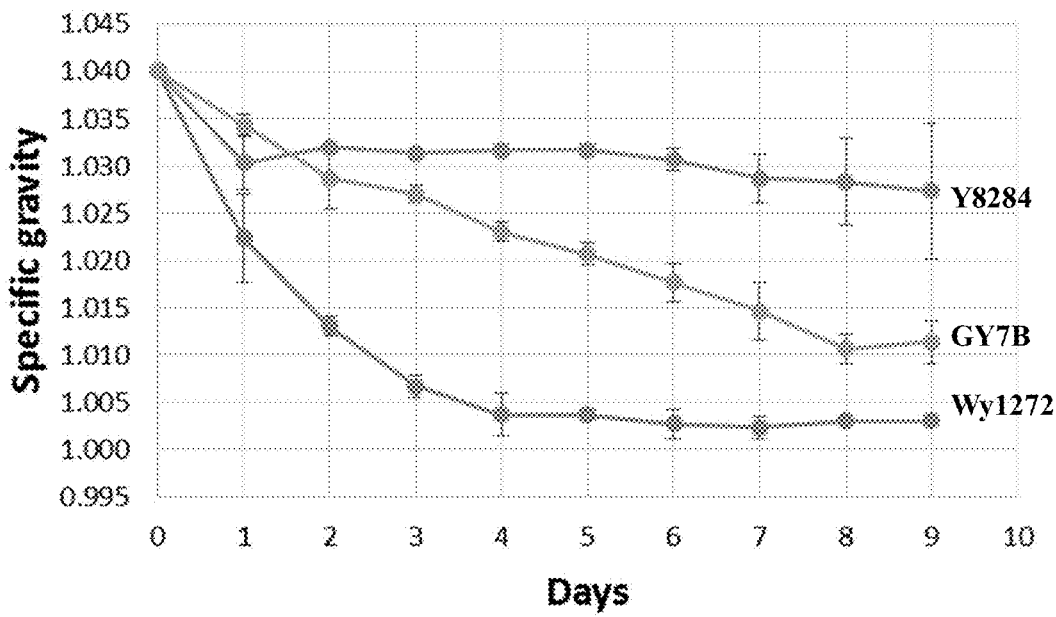
FIG. 2C is a graph reporting pH and apparent extract of a brewer's wort using *Saccharomyces cerevisiae* (American Ale II strain; Wyeast 1272), GY7B, and *Lachancea thermotolerans*; type strain NRRL Y-8284. GY7B fermented faster than *L. thermotolerans* but slower than *S. cerevisiae*. GY7B exhibited rapid souring during fermentation, reaching pH 3.5 in 4 days.
Figure 2C:
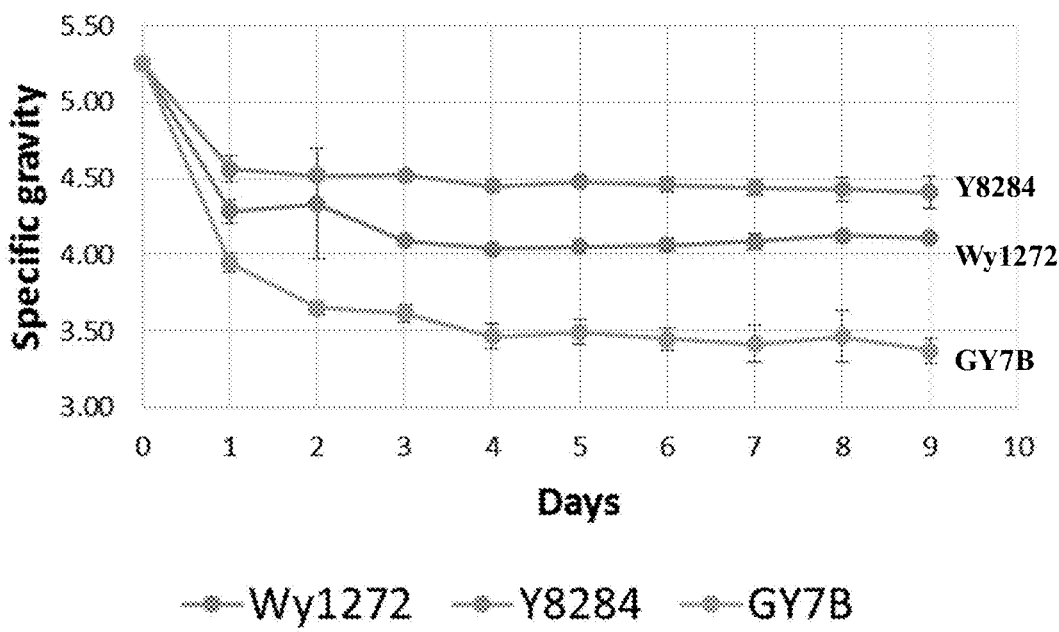

To further examine the fast acidifying properties of GY7B as compared to fermentation by brewer's yeast the fermentation of GY7B was compared to the *L. thermotolarans* type strain, NRRL Y-8284, and a traditional *Saccharomyces cerevisiae* ale strain, American Ale II, Wyeast 1272. Brewer's wort with an original gravity of 1.040 and a pH 5.25 was created at the University of the Sciences pilot brewery. Triplicate fermentations of 400 mL in Erlenmeyer flasks sealed with a fermentation airlock were inoculated with $1\times10^6$ yeast cells/mL/° P. Apparent extract and pH were measured daily at the same time with the averages reported in FIG. 2C. The standard deviation is reported as error bars. As expected, *S. cerevisiae* rapidly ferments the wort to a final gravity of 1.003 in 4 days. The apparent extract of the wort fermented by *L. thermotolerans* is only 1.027 after 9 days of fermentation. GY7B ferments slowly but gradually reaching 1.011 apparent attenuation after 9 days. Fermentation was not yet complete after 9 days in this trial as final gravity with GY7B in other fermentations was observed to be about 1.001. Most importantly, the pH of these pilot fermentations indicated the rapid acidifying power of GY7B as the pH reached 3.5 after only 4 days. The pH of the *S. cerevisiae* beer reached 4.1 after 9 days of fermentation and *L. thermotolerans* only reached 4.4.

These data demonstrate that that GY7B and the *L. thermotolerans* type strain NRRL Y-8284 are phenotypically distinct and that GY7B is capable of rapid sour fermentation of beer.

Example 3: Morphological Comparison of *Lachancea Thermotolerans* and GY7B

Figure 3A:
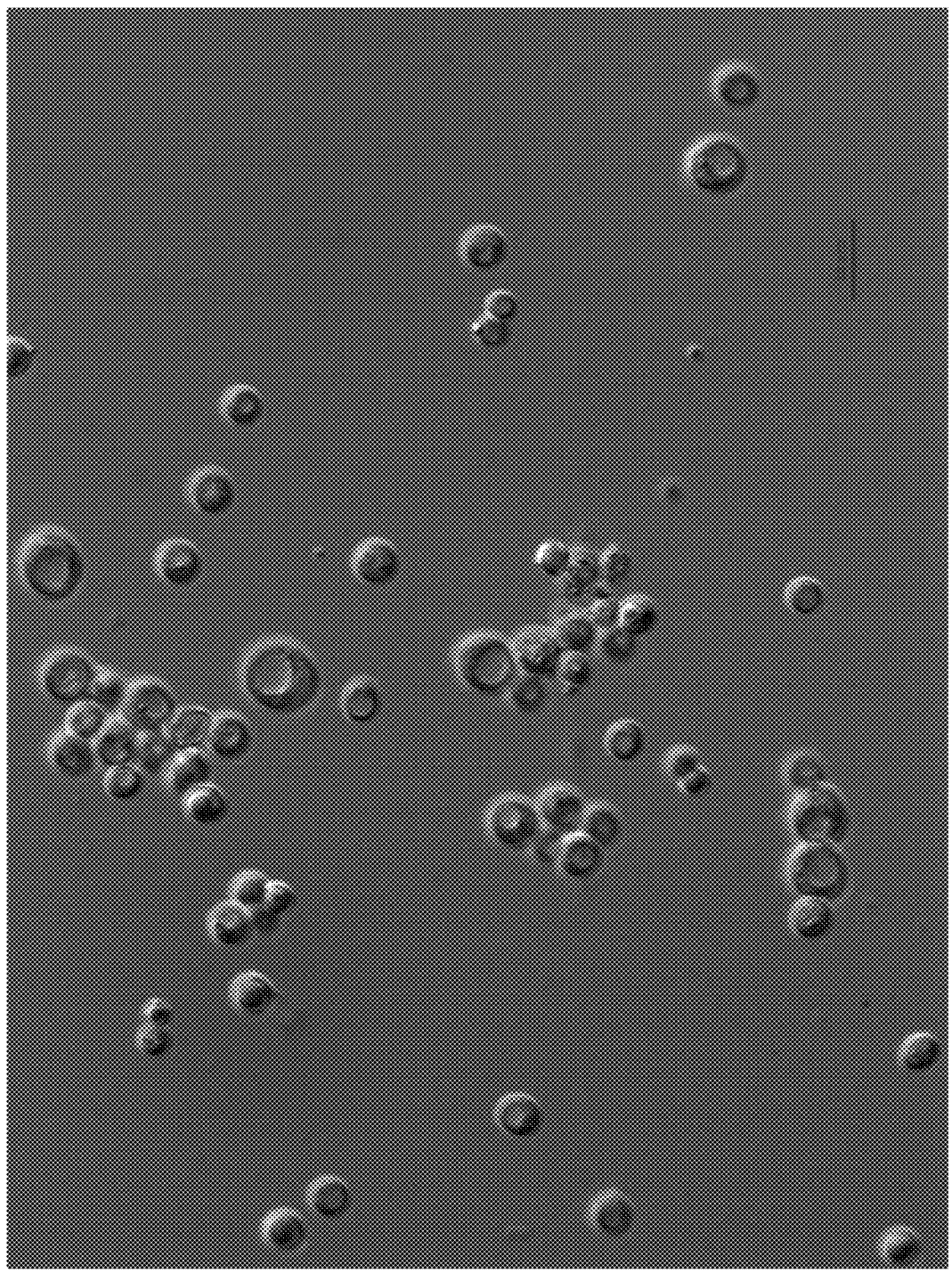
FIGS. 3A-3B are images comparing the morphology of GY7B (FIG. 3A) and standard *Lachancea thermotolerans*; NRRL Y-8284 (FIG. 3B) yeast. Cultures were grown in yeast extract peptone dextrose (YPD) agar for 72 hours at 25° C. and visualized under differential interference microscopy. Utilizing ImageJ, the average length of GY7B=4.6±0.607 µm and Y8284=6.9±0.934 µm.
Figure 3B:
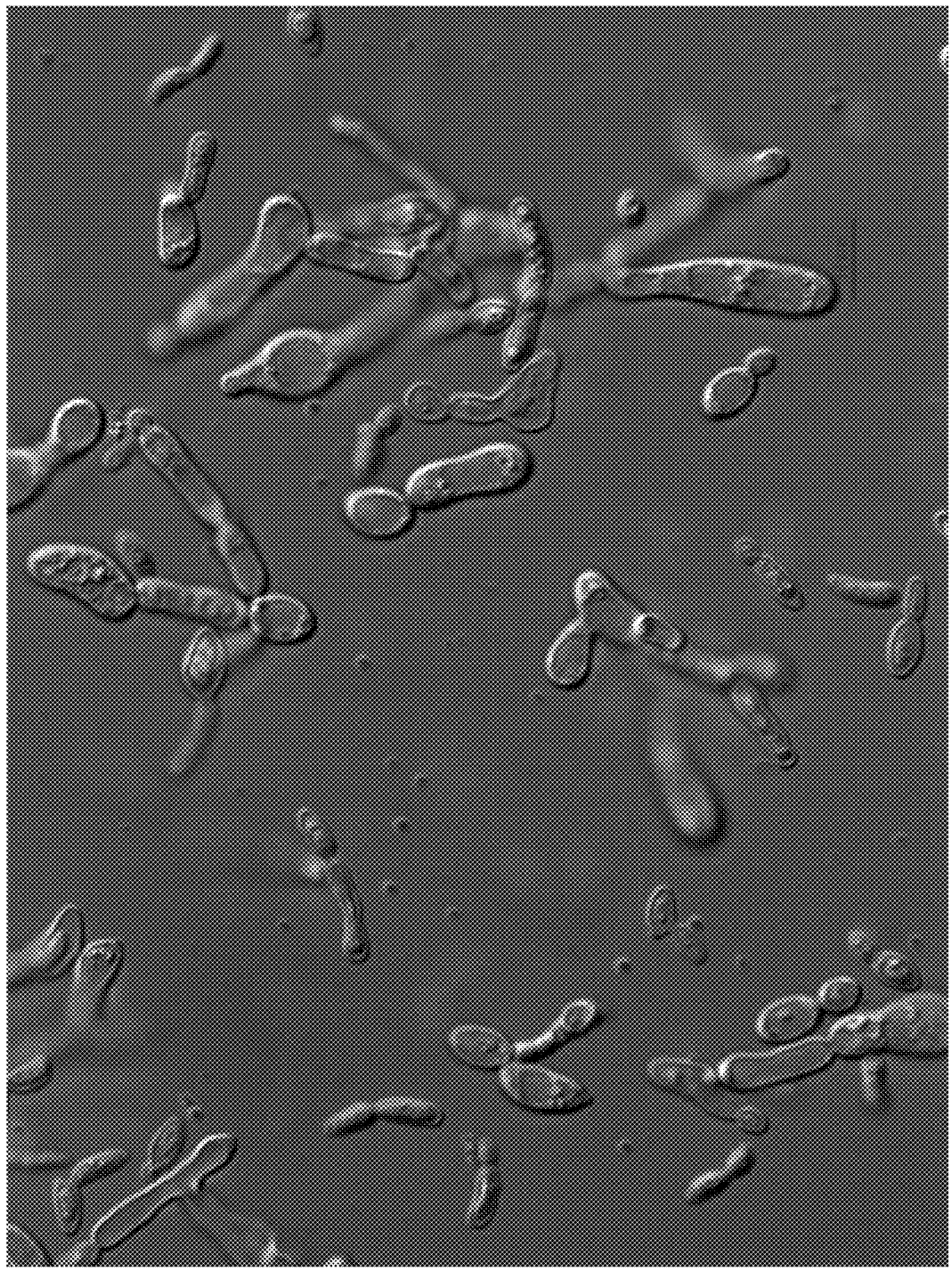
Figure 4A:
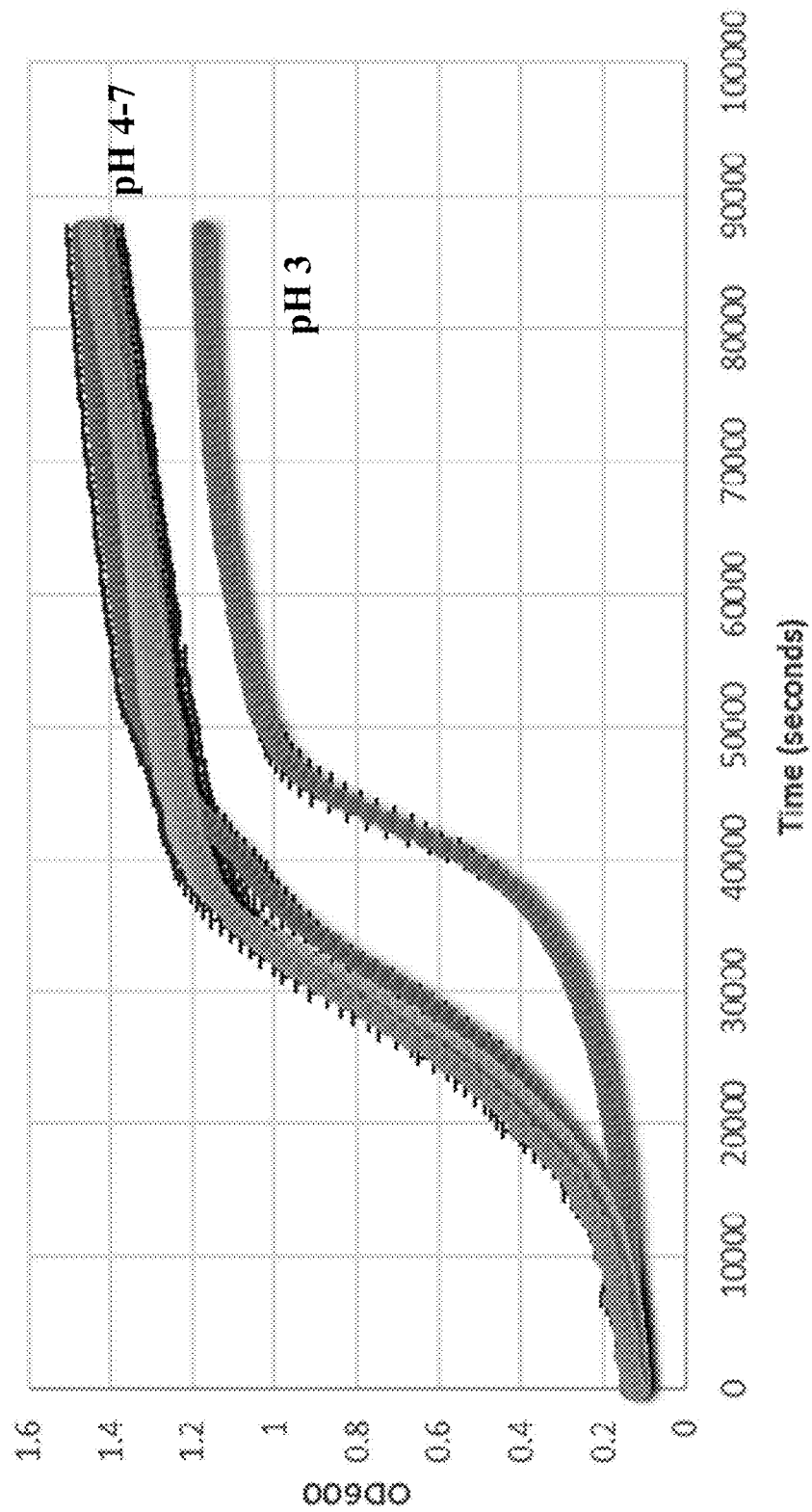
FIGS. 4A-4B are graphs showing the effect of pH on growth rates for GY7B (FIG. 4A) and standard *Lachancea thermotolerans*; NRRL Y-8284 (FIG. 4B) yeast over time. GY7B exhibited greater tolerance for low pH than *L. thermotolerans*.
Figure 4B:
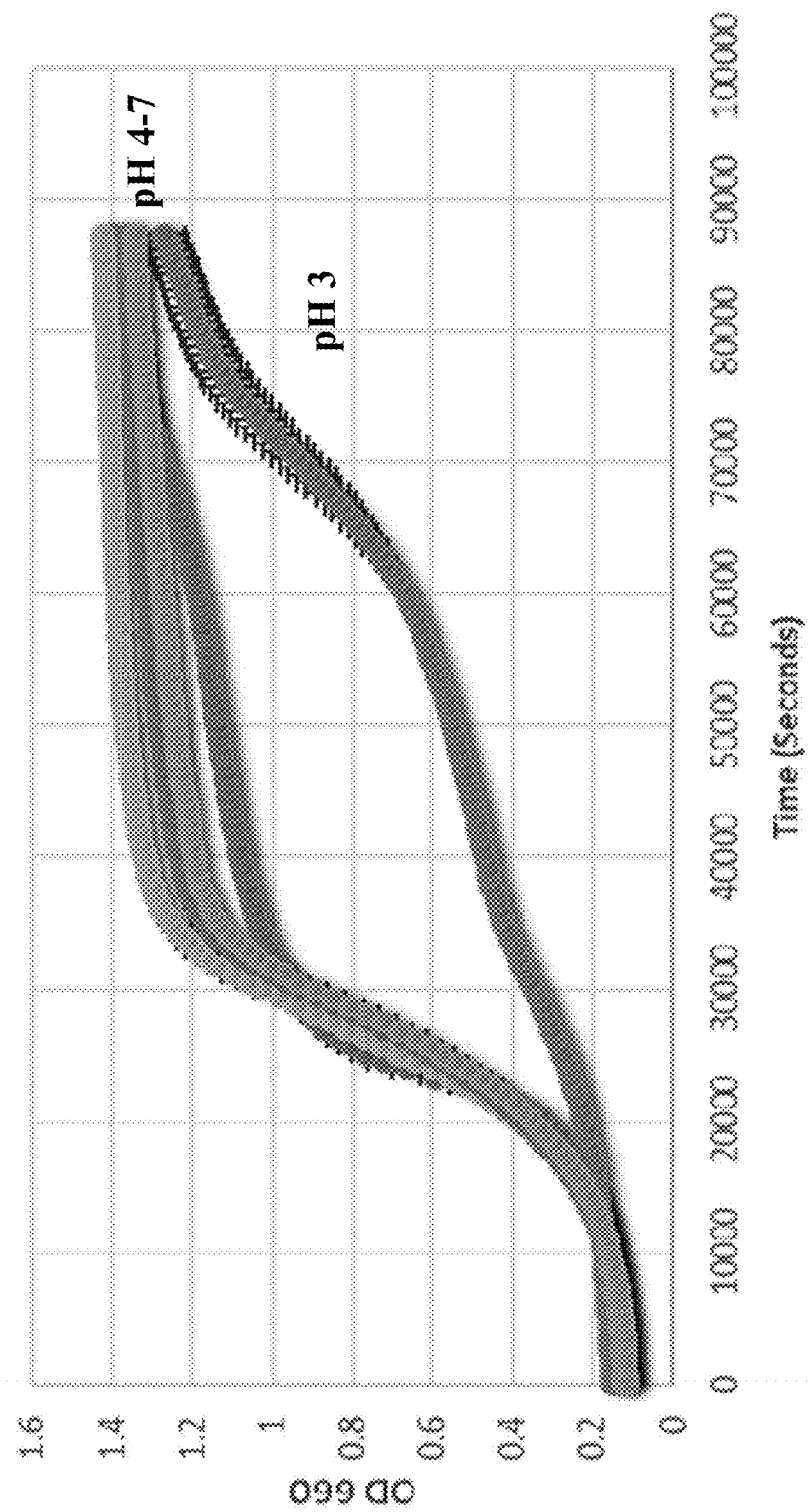

To further illustrate the phenotypic differences between GY7B and *L. thermotolerans* cellular morphology was compared. Cultures of GY7B (FIG. 3A) or *L. thermotolerans* (FIG. 3B) were grown in yeast extract peptone dextrose (YPD) agar for 72 hours at 25° C. and visualized under differential interference microscopy. Utilizing the software ImageJ (NIH) to measure cell size, the length average of GY7b is 4.6±0.607 μm and Y8284 is 6.9±0.934 μm.

Example 4: pH and Ethanol Tolerance of GY7B

Figure 5A:
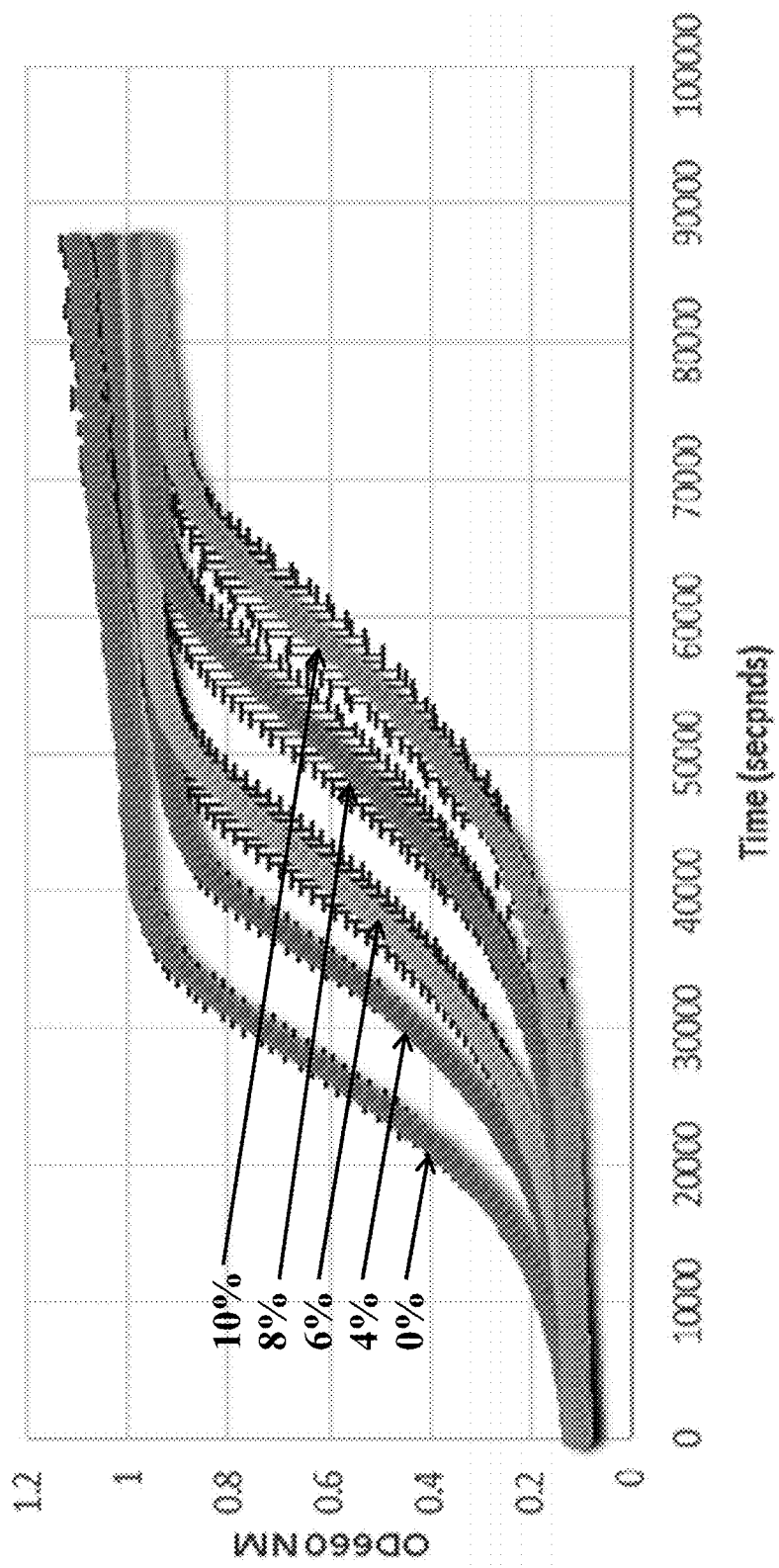
FIGS. 5A-5B are graphs showing effect of ethanol concentration on growth rates for GY7B (FIG. 5A) and *Lachancea thermotolerans* NRRL Y8284 (FIG. 5B) yeast over time. GY7B exhibited greater tolerance for high ethanol concentrations than *L. thermotolerans*.
Figure 5B:
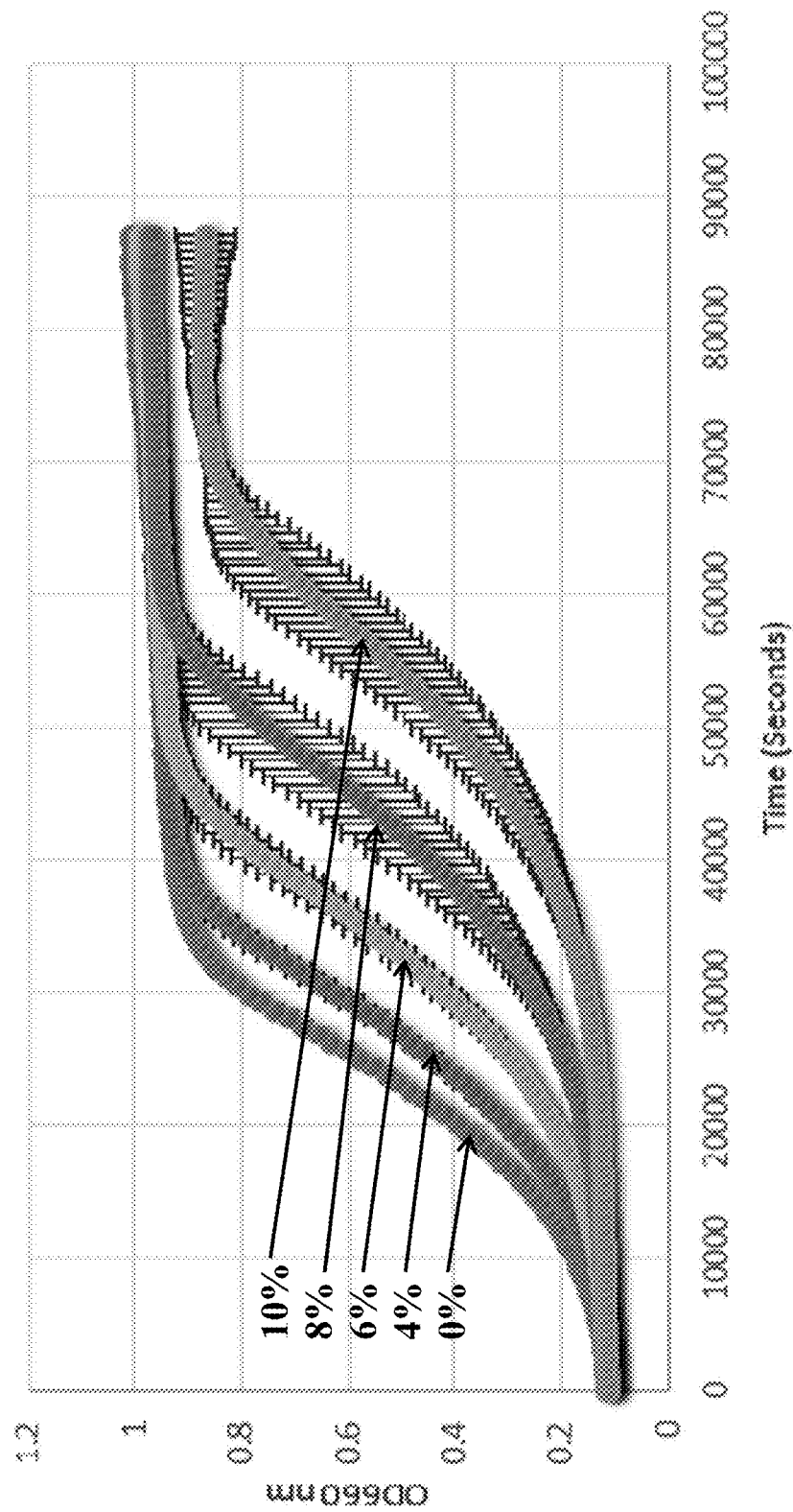

The pH and ethanol tolerance of GY7B and *L. thermotolerans* were evaluated by measuring growth at variable pH (FIG. 4A-5B) or ethanol percentages (v/v) (FIG. 5A-5B). Freshly cultured yeast were propagated in 5 mL of YPD, shaken at 180 rpm at 30° overnight. A spectrophotometer was used to measure the $OD_{600}$ and the culture was diluted with fresh YPD to reach an $OD_{600}$ of 0.1. For ethanol tolerance, each sample was spiked with 100% Ethanol to reach a final concentration of 0%, 4%, 6%, 8%, or 10% (v/v). For pH the YPD was acidified with Hydrochloric acid to cover a pH range from 3-7 which was then used to re-suspend yeast after centrifugation. 200 μL of $OD_{600}$=0.1 culture was placed in a well of a clear, round-bottom 96-well plate (Corning). A TECAN fluorimeter was used to read the $OD_{600}$ every 5 minutes. Throughout the experiment the fluorimeter was held at 30° with 4 minutes of orbital shaking at 120 rpm and 1 minute of linear shaking at 270 rpm in between each read. All samples were done in triplicate with the average values reported. The standard deviation is displayed as error bars. GY7B is more acid tolerant and ethanol tolerant than *L. thermotolerans*. Both GY7B and *L. thermotolerans* can proliferate in up to 10% ethanol (v/v).

Example 5: Genetic Sequencing of GY7B and Comparison to *Lachancea thermotolerans*

To further examine genotypic differences between *L. thermotolerans* and GY7B, the sequences of the ITS region of the rDNA and the actin1 gene from GY7B were examined. Primers specific for each region were used in a PCR reaction. The sequences were resolved via gel electrophoresis. Amplicons were then excised, purified, and sent for sequencing. The resultant sequences were validated and analyzed with BLAST. *L. thermotolerans* NRRL Y8284 and GY7B differ by 2 nt in the ITS region and 7 nt in the actin1 gene. The consensus sequences are listed below. Coupled with the extensive phenotypic differences between GY7B and the *L. thermotolerans* type strain, this evidence strongly suggests that GY7B is a novel species of the *Lachancea* genus.

TABLE 2

Nucleotide differences between *L. thermotolerans* NRRL Y8284 and GY7B

| Genetic Region | NCBI reference sequence | nt differences with GY7B query |
|---|---|---|
| D1/D2 | XR_002432227.1 | 0 |
| ITS | KY104005.1 | 2 |
| actin1 | XM_002555799.1 | 7 |

>GY7B D1D2: SEQ ID NO. 7:
ACGGCGAGTGAAGCGGCAAAAGCTCAAATTTGAAATCTGGCACCTTCGGTG
TCCGAGTTGTAATTTGAAGAAGCTACTTTGGGGCTAGTCCTTGTCTATGTT
CCTTGGAACAGGACGTCATGGAGGGTGAGAATCCCGTATGGCGAGGAGTCT
AGTCCTATGTAAAGTGCTTTCGACGAGTCGAGTTGTTTGGGAATGCAGCTC
TAAGTGGGTGGTAAATTCCATCTAAAGCTAAATATTGGCGAGAGACCGATA
GCGAACAAGTACAGTGATGGAAAGATGAAAAGAACTTTGAAAAGAGAGTGA
AAAAGTACGTGAAATTGTTGAAAGGGAAGGGCATTTGATCAGACATGGTGT
TTTGCGACCCTCGCTCCTTGTGGGTGGGGATCTCGCAGCTCACTGGGCCAA
CATCAGTTTTGGCGGTAGGATAAATCTTTGGGAACGTGGCTTGTCTTCGGA
GAAGCGTTATAGCCCAGGGGAATACTGCCAGCCGGGACTGAGGACTGCGAC
TTT

>GY7B ITS: SEQ ID NO. 8:
GTTAGAGCAGCCGGGAAGTTCAGGAGCCTGCGCTTGATTGCGCGGCCGATG
ATGCTTTCTGTTAACGACTGTCTCTCTACACACACACTGTGGAGTAATTTA
TTTTACAACGCTTCTTCTTTGGGCTTTACGGCCCAAGGGTTACAAACACAA
ACAACTATTGTATTTTAAACATTGTCAATTATTTTTCATTTTAGAAAAAAA
ATATTTAAAACTTTCAACAACGGATCTCTTGGTTCTCGCATCGATGAAGAA
CGCAGCGAAATGCGATAAGTATTGTGAATTGCAGATATTCGTGAATCATCG
AATCTTTGAACGCACATTGCGCCCTCTGGTATTCCAGGGGGCATGCCTGTT
TGAGCGTCATTTCCTTCTCAAACCCTCGGGTTTGGTAGTGAGTGGTACTCT
TTCTGGGTTAACTTGAAAATGCTGGCCATCTGGCTGTTGCTGACTGAGGTT
TTAGTCCAGTCCGCTGATACTCTGCGTATTAGGTTTTACCAACTCGTAGTG
GCGTTAGTAGGCGTTTTAAAGGCTTTTACTGAAAGTACAGACAGTCTGGCA
AACAGTATTCATAAAGTTT

>GY7B actin1: SEQ ID NO. 9:
GCTCAGTCCAAGAGAGGTATCTTGACCCTGCGTTACCCTATCGAGCACGGT
ATCGTCACCAACTGGGACGACATGGAGAAGATCTGGCATCACACCTTCTAC
AACGAGCTGAGAGTGGCCCCAGAGGAGCACCCAGTCTTGTTGACCGAGGCC
CCAATGAACCCTAAGTCCAACAGAGAGAAGATGACTCAGATCCTGTTCGAG
ACCTTCAACGTTCCAGCCTTCTACGTCTCCATCCAGGCCGTCTTATCCCTG
TACTCCTCTGGTAGAACCACCGGTATCGTCTTGGACTCCGGTGACGGTGTT
ACTCACGTTGTGCCAATCTACGCCGGTTTCTCCTTGCCTCACGGTATCTTG
AGAATCGACTTGGCTGGTAGAGACATGACCGACTACTTGATGAAGATCTTG
AGTGAGCGTGGCTACTCTTTCTCCACAACCGCCGAGAGAGAAATCGTGCGT -continued

```
GACATCAAGGAGAAGTTGTGTTACGTCGCCTTGGACTTCGAGCAAGAGATG

CAGACCGCTGCCCAGTCCTCTGCCATTGAGAAGTCTTACGAGTTGCCTGAC

GGCCAAGTCATCACCATCGGTAACGAGAGATTCAGAGCCCCAGAGGCCCTG

TTCCACCCAAGTCTGCTGGGTCTGGAAGCTGCTGGTATCGACCAGACTGCT

TACAACTCTATCATGAAGTGTGACGTCGACGTCCGTAAGGAGTTGTACGGT

AATATCGTCATGTCTGGTGGTACCACCATGTTCCCAGGTATTGCCGAGAGA

ATGCAGAAGGAAATCACTGCTTTGGCTCCATCCTCCATGAAGGTGAAGATC

ATTGCCCCACCAGAGAGAAAGTACTCTGTCTGGATCGGTGGTTCTA
```

Example 6: Sugar Assimilation Assay

Comparison of sugar assimilation between *L. thermotolerans* NRRL Y8284 and GY7B was performed using YT Microplates (BIOLOG®). Freshly propagated yeast colonies on YPD agar were selected 48-72 hours after growth at 25-30° C. A single colony was inoculated into 15 mL of sterile water and was adjusted as needed to yield a % transmittance of 47% ±2% as determined by spectrophotometer. 100 μL was then placed in each of the 96 wells of the YT Microplate. The plate was incubated at 27° C. in a humidified chamber for about 3 days and the results were interpreted by visual inspection. To validate the results, each experiment was repeated twice by two independent analysts. Shown in Table 3 are the consensus results. An empty lane indicates no growth, a single (+) indicates weak growth, and a triple (+++) indicates strong growth. Table 3 is arranged according to the design of the YT Microplate. The first three rows, shown in bold, are oxidation tests that utilize a patented color change in response to yeast cell metabolism. The remaining wells are growth assimilation tests in which turbidity of the well is recorded. Table 3 demonstrates the metabolic and assimilation differences between GY7B and *L. thermotolerans*.

TABLE 3

| | water | acetic acid | formic acid | propionic acid | succinic acid | succinic acid mono-methyl ester |
|---|---|---|---|---|---|---|
| GY7B | | + | ++ | + | + | |
| *L. thermotolerans* | | | | | | |

| | d-cellobiose | gentiobiose | maltose | maltotriose | d-melezitose | d-melibiose |
|---|---|---|---|---|---|---|
| GY7B | + | + | +++ | + | + | |
| *L. thermotolerans* | | + | + | | | |

| | n-acetyl-d-glucosamine | α-d-glucose | d-galactose | d-psicose | l-sorbose | salicin |
|---|---|---|---|---|---|---|
| GY7B | | +++ | + | + | | |
| *L. thermotolerans* | | + | | | | |

| | water | fumaric acid | l-malic acid | succinic acid mono-methyl ester | bromo-succinic acid | l-glutamic acid |
|---|---|---|---|---|---|---|
| GY7B | | ++ | ++ | + | + | + |
| *L. thermotolerans* | | + | + | | + | + |

| | d-cellobiose | gentiobiose | maltose | maltitriose | d-melezitose | d-melibiose |
|---|---|---|---|---|---|---|
| GY7B | + | + | ++ | ++ | ++ | ++ |
| *L. thermotolerans* | + | + | + | + | + | + |

| | n-acetyl-d-glucosamine | d-glucosamine | α-d-glucose | d-galactose | d-psicose | l-rhamnose |
|---|---|---|---|---|---|---|
| GY7B | + | + | ++ | ++ | + | +++ |
| *L. thermotolerans* | + | + | + | | + | + |

| | maltitol | d-mannitol | d-sorbitol | adonitol | d-arabitol | xylitol |
|---|---|---|---|---|---|---|
| GY7B | ++ | ++ | ++ | ++ | ++ | + |
| *L. thermotolerans* | + | ++ | + | | + | ++ |

| | d-xylose | succinic acid mono-methyl ester plus d-xylose | n-acetyl-l-glutamic acid plus d-xylose | quinic acid plus d-xylose | d-glucuronic acid plus d-xylose | dextrin plus d-xylose |
|---|---|---|---|---|---|---|
| GY7B | ++ | +++ | ++ | ++ | ++ | ++ |
| *L. thermotolerans* | ++ | +++ | + | + | + | ++ |

| | l-aspartic acid | l-glutamic acid | l-proline | d-gluconic acid | dextrin | inulin |
|---|---|---|---|---|---|---|
| GY7B | ++ | + | + | ++ | + | ++ |
| *L. thermotolerans* | | | | | | |

TABLE 3-continued

|  | palantinose | d-raffinose | stachyose | sucrose | d-trehalose | turanose |
|---|---|---|---|---|---|---|
| GY7B | +++ | + | + | +++ | +++ | +++ |
| L. thermotolerans | + | + | + | + |  | + |

|  | d-mannitol | d-sorbitol | d-arabitol | xylitol | glycerol | tween 80 |
|---|---|---|---|---|---|---|
| GY7B | + | + | + | + | + |  |
| L. thermotolerans |  |  |  |  |  |  |

|  | γ-amino-butyric acid | α-keto-glutaricacid | 2-keto-d-gluconic acid | d-gluconic acid | dextrin | inulin |
|---|---|---|---|---|---|---|
| GY7B | + | ++ | + | + | ++ | ++ |
| L. thermotolerans | ++ | ++ |  |  | ++ | ++ |

|  | palantinose | d-raffinose | stachyose | sucrose | d-trehalose | turanose |
|---|---|---|---|---|---|---|
| GY7B | ++ | ++ | ++ | + | ++ | ++ |
| L. thermotolerans | ++ | + | + | + | + | + |

|  | l-sorbose | α-methyl-d-glucoside | β-methyl-d-glucoside | amygdalin | arbutin | salicin |
|---|---|---|---|---|---|---|
| GY7B | + | ++ | + | ++ | + |  |
| L. thermotolerans | + | + | + | + | + |  |

|  | i-erythritol | glycerol | tween 80 | l-arabinose | d-arabinose | d-ribose |
|---|---|---|---|---|---|---|
| GY7B | + | + | + | ++ | ++ | +++ |
| L. thermotolerans | ++ | + | + | ++ | ++ | +++ |

|  | α-d lactose plus-xylose | d-melibiose plus d-xylose | d-galatose plus d-xylose | m-inositol plus d-xylose | 1,2-proanediol plus d-xylose | acetoin plus d-xylose |
|---|---|---|---|---|---|---|
| GY7B |  | + | + | + | + | ++ |
| L. thermotolerans | + | + | + | + | + | + |

Example 7: Flocculation

Figure 6:
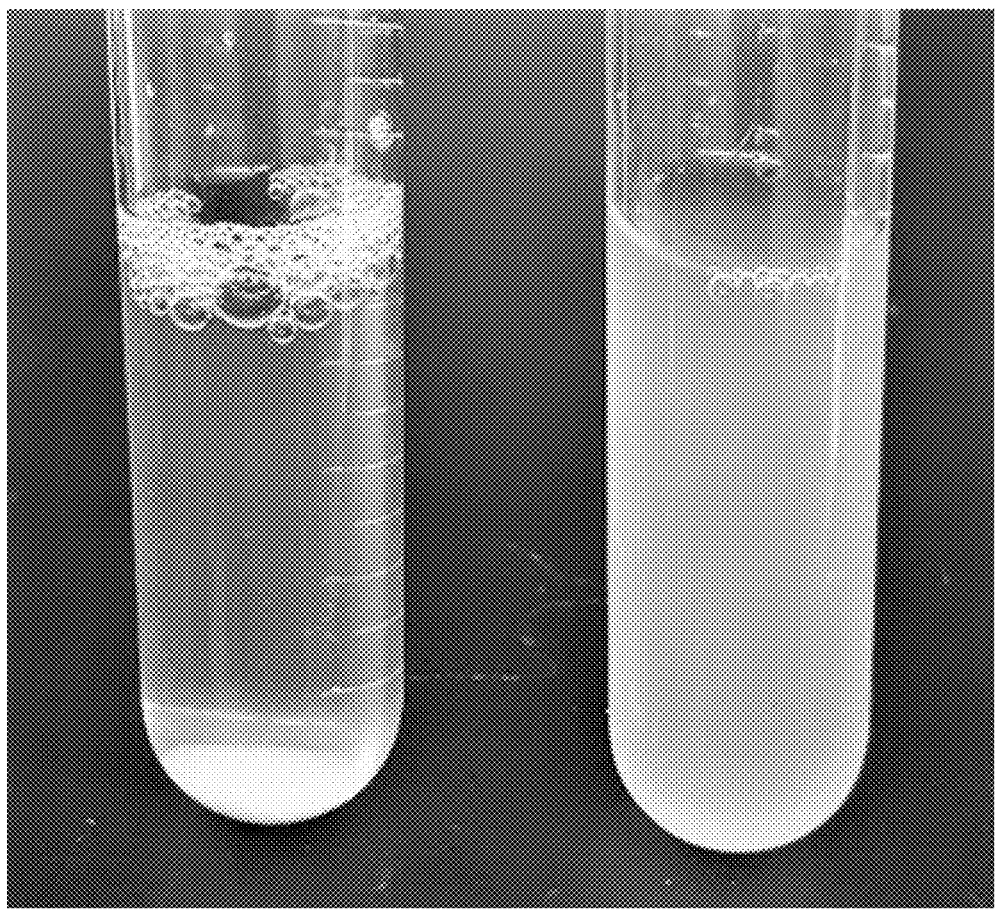
FIG. 6 is an image comparing the flocculation characteristics of GY7B and standard *Lachancea thermotolerans*; NRLL Y-8284. GY7B is highly flocculant while *L. thermotolerans* is not.

To compare the flocculation ability of GY7B and *L. thermotolerans* a freshly grown colony on YPD agar was selected for propagation in 5 mL of laboratory wort. Each was cultured at 250 with no shaking for 7 days. Both tubes were then swirled simultaneously and consistently by hand to evaluate the impact on resuspension of the yeast pellet. *L. thermotolerans* exhibits low flocculation as demonstrated by its dispersed pellet and cloudy beer. GY7B is highly flocculant as demonstrated by its remaining pellet and clear beer (FIG. 6). The high flocculation ability of GY7B will greatly assist yeast removal after fermentation of beer, enabling more effective centrifugation, filtration, pasteurization or any other stabilizing/clarifying processes post-fermentation.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A kit comprising:
a yeast strain from the genus *Lachancea*, wherein the yeast strain comprises at least one of: the nucleotide sequence of SEQ ID NO: 8 within the ITS region; the nucleotide sequence of SEQ ID NO: 9 within the actin1 gene; and
instructional materials comprising instructions for producing a yeast-fermented beverage using the yeast strain.

2. The kit of claim 1, wherein the kit further comprises one or more items or ingredients to produce a yeast-fermented beverage using the yeast strain, and wherein the one or more items or ingredients comprise one or more items selected from the group consisting of:
prepared wort solution; dry malt extract; one or more grains selected from the group consisting of barley, wheat, corn, rye, rice, oats, sorghum, millet, buckwheat, quinoa, and teff; at least one additional yeast strain selected from the group consisting of *Saccharomyces cerevisiae, Saccharomyces pastorianus, Saccharomyces paradoxus, Saccharomyces eubayanus, Saccharomyces ludwigii, Aureobasidium pullulans, Cyberlindnera saturnus, Hansensiaspora uvarum, Hansenisaspora guilliermondii, Hansensiaspora osmophila, Hansensiasporavineae, Hansenula anomala, Issatchenkia occidentalis, Issatchenkia orientalis, Pichia kluyveri, Pichia caribbica, Pichia fermentans, Pichia kudriavzevii, Pichia Membranifaciens, Rhodotorula mucilaginosa, Torulaspora delbrueckii, Candida colliculosa, Candida shehatae, Candida tropicalis, Candida ethanolica, Candida krusei, Candida magnolia, Candida milleri, Clavispora lusitaniae, Wickerhamomyces subpelliculosus, Wickerhamomyces anomalus, Zygosaccharomyces rouxii, Zygosaccharomyces bailii, Zygosaccharomyces fermentati, Zygosaccharomycesflorentinus, Kluyveromyces lactis, Kluyveromyces marxianus, Lachancea thermotolerans, Brettanomyces bruxellensis, Brettanomyces anomalus, Brettanomyces custersianus, Brettanomyces naardenensis, Brettanomyces nanus, Dekkera bruxellensis*, and *Dekkera anomala*; one or more varieties of hops; conditioned brewing water; and one or more sugar adjuncts.

3. The kit of claim 1, wherein the yeast strain is able to produce a yeast-fermented beverage with a pH of about 4.2 to about 3.3 without the use of lactic acid producing bacteria.

4. The kit of claim 1, wherein the yeast-fermented beverage is beer.

5. The kit of claim 1, wherein the yeast strain, when used to ferment a wort according to the instructional materials, is able to reduce the pH of the wort to about 3.5 in about 5 days without the use of acid producing bacteria.

6. The kit of claim 1, wherein the yeast strain is GY7B (deposited with the ATCC under Accession Number PTA-125167 on Jul. 19, 2018).

7. The kit of claim 1, wherein the yeast strain comprises the nucleotide sequence of SEQ ID NO: 8 within the ITS region.

8. The kit of claim 1, wherein the yeast strain comprises the nucleotide sequence of SEQ ID NO: 9 within the actin1 gene.

9. The kit of claim 1, wherein the yeast strain comprises the nucleotide sequence of SEQ ID NO: 8 within the ITS region and the nucleotide sequence of SEQ ID NO: 9 within the actin1 gene.

10. The kit of claim 1, wherein the yeast produces a yeast-fermented beverage with a pH of about 4.2 to about 3.3 when used according to the instructional materials.

11. The kit of claim 1, wherein the instructional materials instruct to ferment a wort with the yeast strain in the absence of any acid producing bacteria.

12. The kit of claim 1, wherein the instructional materials instruct to ferment a wort with the yeast strain in the absence of any lactic acid producing bacteria.

13. The kit of claim 1, wherein the instructional materials instruct to ferment a wort with the yeast strain in the absence of bacteria belonging to genera *Lactobacillus* or *Pediococcus*.

14. The kit of claim 1, wherein the instructional materials instruct to ferment a wort comprising malt derived from one or more grains selected from the group consisting of barley, wheat, corn, rye, rice, oats, sorghum, millet, buckwheat, quinoa, and teff with the yeast strain.

15. The kit of claim 1, wherein the instructional materials instruct to ferment a wort with the yeast in the presence of at least one additional yeast strain selected from the group consisting of *Saccharomyces cerevisiae, Saccharomyces pastorianus, Saccharomyces paradoxus, Saccharomyces eubayanus, Saccharomyces ludwigii, Aureobasidium pullulans, Cyberlindnera saturnus, Hansensiaspora uvarum, Hansensiaspora guilliermondii, Hansensiaspora osmophila, Hansensiasporavineae, Hansenula anomala, Issatchenkia occidentalis, Issatchenkia orientalis, Pichia kluyveri, Pichia caribbica, Pichia fermentans, Pichia kudriavzevii, Pichia Membranifaciens, Rhodotorula mucilaginosa, Torulaspora delbrueckii, Candida colliculosa, Candida shehatae, Candida tropicalis, Candida ethanolica, Candida krusei, Candida magnolia, Candida milleri, Clavispora lusitaniae, Wickerhamomyces subpelliculosus, Wickerhamomyces anomalus, Zygosaccharomyces rouxii, Zygosaccharomyces bailiff, Zygosaccharomyces fermentati, Zygosaccharomycesflorentinus, Kluyveromyces lactis, Kluyveromyces marxianus, Lachancea thermotolerans, Brettanomyces bruxellensis, Brettanomyces anomalus, Brettanomyces custersianus, Brettanomyces naardenensis, Brettanomyces nanus, Dekkera bruxellensis*, and *Dekkera anomala*.

16. The kit of claim 15, wherein the wort further comprises a hops.

17. The kit of claim 16, wherein the hops comprises at least one selected from the group consisting of Ahtanum, Amarillo, Apollo, Cascade, Centennial, Chinook, Citra, Cluster, Columbus, Crystal, Eroica, Galena, Glacier, Greenburg, Horizon, Liberty, Millenium, Mount Hood, Mount Rainier, Newport, Nugget, Palisade, Santiam, Simcoe, Sterling, Summit, Tomahawk, Ultra, Vanguard, Warrior, Willamette, Zeus, Admiral, Brewer's Gold, Bullion, Challenger, First Gold, Fuggles, Goldings, Herald, Northdown, Northern Brewer, Phoenix, Pilot, Pioneer, Progress, Target, Whitbread Golding Variety (WGV), Hallertau, Hersbrucker, Saaz, Tettnang, Spalt, Feux-Coeur Francais, Galaxy, Green Bullet, Motueka, Nelson Sauvin, Pacific Gem, Pacific Jade, Pacifica, Pride of Ringwood, Riwaka, Southern Cross, Lublin, Magnum, Perle, Polnischer Lublin, Saphir, Satus, Select, Strisselspalt, Styrian Goldings, Tardif de Bourgogne, Tradition, Bravo, Calypso, Chelan, Comet, El Dorado, San Juan Ruby Red, Satus, Sonnet Golding, Super Galena, Tillicum, Bramling Cross, Pilgrim. Hallertauer Herkules, Hallertauer Magnum, Hallertauer Taurus, Merkur, Opal, Smaragd, Halleratau Aroma, Kohatu, Rakau, Stella, Sticklebract, Summer Saaz, Super Alpha, Super Pride, Topaz, Wai-iti, Bor, Junga, Marynka, Premiant, Sladek, Styrian Atlas, Styrian Aurora, Styrian Bobek, Styrian Celeia, Sybilla, and Sorachi Ace.

18. The kit of claim 1, wherein the instructional materials instruct not to use lactic acid while producing a yeast-fermented beverage.

19. The kit of claim 1, wherein the instructional materials instruct not to add lactic acid to a wort, before, during, or after fermentation.

* * * * *

UNITED STATES PATENT AND TRADEMARK OFFICE
CERTIFICATE OF CORRECTION

PATENT NO. : 12,054,696 B2
APPLICATION NO. : 17/706365
DATED : August 6, 2024
INVENTOR(S) : Farber Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 204 days.

Signed and Sealed this
Twenty-eighth Day of January, 2025

Coke Morgan Stewart
*Acting Director of the United States Patent and Trademark Office*

SEQUENCE LISTING

```
<160> NUMBER OF SEQ ID NOS: 12

<210> SEQ ID NO 1
<211> LENGTH: 24
<212> TYPE: DNA
<213> ORGANISM: Artificial Sequence
<220> FEATURE:
<223> OTHER INFORMATION: Chemically synthesized

<400> SEQUENCE: 1
gcatatcaat aagcggagga aaag                                           24

<210> SEQ ID NO 2
<211> LENGTH: 19
<212> TYPE: DNA
<213> ORGANISM: Artificial Sequence
<220> FEATURE:
<223> OTHER INFORMATION: Chemically synthesized
```

```
<400> SEQUENCE: 2
ggtccgtgtt tcaagacgg                                                  19

<210> SEQ ID NO 3
<211> LENGTH: 19
<212> TYPE: DNA
<213> ORGANISM: Artificial Sequence
<220> FEATURE:
<223> OTHER INFORMATION: Chemically synthesized

<400> SEQUENCE: 3
tccgtaggtg aacctgcgg                                                  19

<210> SEQ ID NO 4
<211> LENGTH: 20
<212> TYPE: DNA
<213> ORGANISM: Artificial Sequence
<220> FEATURE:
<223> OTHER INFORMATION: Chemically synthesized

<400> SEQUENCE: 4
tcctccgctt attgatatgc                                                 20

<210> SEQ ID NO 5
<211> LENGTH: 23
<212> TYPE: DNA
<213> ORGANISM: Artificial Sequence
<220> FEATURE:
<223> OTHER INFORMATION: Chemically synthesized

<400> SEQUENCE: 5
attgataacg gttccggtat gtg                                             23

<210> SEQ ID NO 6
<211> LENGTH: 27
<212> TYPE: DNA
<213> ORGANISM: Artificial Sequence
<220> FEATURE:
<223> OTHER INFORMATION: Chemically synthesized

<400> SEQUENCE: 6
tcgtcgtatt cttgctttga gatccac                                         27

<210> SEQ ID NO 7
<211> LENGTH: 513
<212> TYPE: DNA
<213> ORGANISM: Artificial Sequence
<220> FEATURE:
<223> OTHER INFORMATION: Chemically synthesized

<400> SEQUENCE: 7
acggcgagtg aagcggcaaa agctcaaatt tgaaatctgg caccttcggt gtccgagttg     60
taatttgaag aagctacttt ggggctagtc cttgtctatg ttccttggaa caggacgtca    120
tggagggtga gaatcccgta tggcgaggag tctagtccta tgtaaagtgc tttcgacgag    180
tcgagttgtt tgggaatgca gctctaagtg ggtggtaaat tccatctaaa gctaaatatt    240
ggcgagagac cgatagcgaa caagtacagt gatggaaaga tgaaagaac tttgaaaaga    300 gagtgaaaaa gtacgtgaaa ttgttgaaag ggaagggcat ttgatcagac atggtgtttt    360
gcgaccctcg ctccttgtgg gtggggatct cgcagctcac tgggccaaca tcagttttgg    420
cggtaggata aatctttggg aacgtggctt gtcttcggag aagcgttata gcccagggga    480
```

| atactgccag ccgggactga ggactgcgac ttt | 513 |

<210> SEQ ID NO 8
<211> LENGTH: 580
<212> TYPE: DNA
<213> ORGANISM: Artificial Sequence
<220> FEATURE:
<223> OTHER INFORMATION: Chemically synthesized

<400> SEQUENCE: 8

| gttagagcag ccgggaagtt caggagcctg cgcttgattg cgcggccgat gatgctttct | 60 |
| gttaacgact gtctctctac acacacactg tggagtaatt tattttacaa cgcttcttct | 120 |
| ttgggctttta cggcccaagg gttacaaaca caaacaacta ttgtatttta aacattgtca | 180 |
| attatttttc attttagaaa aaaaatattt aaaactttca acaacggatc tcttggttct | 240 |
| cgcatcgatg aagaacgcag cgaaatgcga taagtattgt gaattgcaga tattcgtgaa | 300 |
| tcatcgaatc tttgaacgca cattgcgccc tctggtattc caggggcat gcctgtttga | 360 |
| gcgtcatttc cttctcaaac cctcgggttt ggtagtgagt ggtactcttt ctgggttaac | 420 |
| ttgaaaatgc tggccatctg gctgttgctg actgaggttt tagtccagtc cgctgatact | 480 |
| ctgcgtatta ggttttacca actcgtagtg gcgttagtag gcgttttaaa ggcttttact | 540 |
| gaaagtacag acagtctggc aaacagtatt cataaagttt | 580 |

<210> SEQ ID NO 9
<211> LENGTH: 862
<212> TYPE: DNA
<213> ORGANISM: Artificial Sequence
<220> FEATURE:
<223> OTHER INFORMATION: Chemically synthesized

<400> SEQUENCE: 9

| gctcagtcca agagaggtat cttgaccctg cgttaccta tcgagcacgg tatcgtcacc | 60 |
| aactgggacg acatggagaa gatctggcat cacaccttct acaacgagct gagagtggcc | 120 |
| ccagaggagc acccagtctt gttgaccgag gccccaatga accctaagtc aacagagag | 180 |
| aagatgactc agatcctgtt cgagaccttc aacgttccag ccttctacgt ctccatccag | 240 |
| gccgtcttat ccctgtactc ctctggtaga accaccggta tcgtcttgga ctccggtgac | 300 |
| ggtgttactc acgttgtgcc aatctacgcc ggtttctcct tgcctcacgg tatcttgaga | 360 |
| atcgacttgg ctggtagaga catgaccgac tacttgatga agatcttgag tgagcgtggc | 420 |
| tactctttct ccacaaccgc cgagagagaa atcgtgcgtg acatcaagga gaagttgtgt | 480 |
| tacgtcgcct tggacttcga gcaagagatg cagaccgctg cccagtcctc tgccattgag | 540 |
| aagtcttacg agttgcctga cggccaagtc atcaccatcg gtaacgagag attcagagcc | 600 |
| ccagaggccc tgttccaccc aagtctgctg ggtctggaag ctgctggtat cgaccagact | 660 |
| gcttacaact ctatcatgaa gtgtgacgtc gacgtccgta aggagttgta cggtaatatc | 720 |
| gtcatgtctg gtggtaccac catgttccca ggtattgccg agagaatgca gaaggaaatc | 780 |
| actgctttgg ctccatcctc catgaaggtg aagatcattg ccccaccaga gagaaagtac | 840 |
| tctgtctgga tcggtggttc ta | 862 |

<210> SEQ ID NO 10
<211> LENGTH: 28
<212> TYPE: DNA
<213> ORGANISM: Artificial Sequence
<220> FEATURE:
<223> OTHER INFORMATION: Chemically synthesized

```
<400> SEQUENCE: 10
ttgttatccg ctcacaattc cacacaac                                           28

<210> SEQ ID NO 11
<211> LENGTH: 60
<212> TYPE: DNA
<213> ORGANISM: Artificial Sequence
<220> FEATURE:
<223> OTHER INFORMATION: Chemically synthesized

<400> SEQUENCE: 11
atggagggtg agaatcccgt atggcgagga gtctagtcct atgtaaagtg ctttcgacga        60

<210> SEQ ID NO 12
<211> LENGTH: 60
<212> TYPE: DNA
<213> ORGANISM: Artificial Sequence
<220> FEATURE:
<223> OTHER INFORMATION: Chemically synthesized

<400> SEQUENCE: 12
gtcgagttgt ttgggaatgc agctctaagt gggtggtaaa ttccatctaa agctaaatat       60
```